US011752070B2

(12) United States Patent
Helm et al.

(10) Patent No.: US 11,752,070 B2
(45) Date of Patent: Sep. 12, 2023

(54) MIXING AND/OR RECONSTITUTION SYSTEM

(71) Applicant: SANOFI, Paris (FR)

(72) Inventors: Sarah Helm, Frankfurt am Main (DE); Peter Nober, Rüsselsheim (DE); Julian Kersting, Rüsselsheim (DE); Florian Hammen, Rüsselsheim (DE)

(73) Assignee: Sanofi, Paris (FR)

( * ) Notice: Subject to any disclaimer, the term of this patent is extended or adjusted under 35 U.S.C. 154(b) by 488 days.

(21) Appl. No.: 16/765,226

(22) PCT Filed: Nov. 16, 2018

(86) PCT No.: PCT/EP2018/081553
§ 371 (c)(1),
(2) Date: May 19, 2020

(87) PCT Pub. No.: WO2019/101645
PCT Pub. Date: May 31, 2019

(65) Prior Publication Data
US 2020/0281815 A1    Sep. 10, 2020

(30) Foreign Application Priority Data
Nov. 21, 2017 (EP) .................................... 17306609

(51) Int. Cl.
*A61J 1/20* (2006.01)

(52) U.S. Cl.
CPC .......... *A61J 1/2096* (2013.01); *A61J 1/2013* (2015.05); *A61J 1/2037* (2015.05); *A61J 1/2048* (2015.05);
(Continued)

(58) Field of Classification Search
CPC .......... A61J 1/2003; A61J 1/20; A61J 1/2013; A61J 1/2037; A61J 1/2089; A61J 3/00;
(Continued)

(56) References Cited

U.S. PATENT DOCUMENTS

| 6,238,372 | B1   | 5/2001 | Zinger et al. | |
| 6,364,865 | B1 * | 4/2002 | Lavi ...... | A61M 5/148 604/411 |
| 2002/0087144 | A1 * | 7/2002 | Zinger .......... | A61J 1/2096 604/905 |
| 2006/0049209 | A1   | 3/2006 | Baker | |

(Continued)

FOREIGN PATENT DOCUMENTS

| CN | 102186447 | 9/2011 |
| JP | 2012-505676 | 3/2012 |

(Continued)

OTHER PUBLICATIONS

International Preliminary Report on Patentability in Application No. PCT/EP2018/081553, dated May 26, 2020, 7 pages.
(Continued)

*Primary Examiner* — Nicholas J. Weiss
*Assistant Examiner* — Seth Han
(74) *Attorney, Agent, or Firm* — Fish & Richardson P.C.

(57) ABSTRACT

The mixing system includes an adaptor, an integrated injection device removably attached to the adaptor comprising a switching element, a first reservoir containing a fluidic first material, and a trigger. The adaptor includes a first attachment location configured to attach a vial. The vial contains a second material within a second reservoir, wherein the second material contains a medicament formulation. The adaptor also includes a first connection element, a flow channel providing fluid communication of the switching element and the first connection element, a sensing arrangement for detecting a pre-defined position of the vial at the first attachment location, and an interlock element which is configured to allow operation of the trigger in order to
(Continued)

establish a fluid communication between the first connection element and the first reservoir only if the sensing arrangement detects the pre-defined position of the vial at the first attachment location.

15 Claims, 21 Drawing Sheets

(52) U.S. Cl.
CPC ............ *A61J 1/2065* (2015.05); *A61J 1/2068* (2015.05); *A61J 2200/70* (2013.01)

(58) Field of Classification Search
CPC ...... A61J 1/2048; A61J 1/2062; A61J 1/2068; A61J 1/2058; A61J 1/2065; A61J 1/2096; A61J 1/201; A61M 5/31511; A61M 5/3129; A61M 5/20; A61M 5/31501; A61M 5/502
See application file for complete search history.

(56) References Cited

U.S. PATENT DOCUMENTS

| | | | |
|---|---|---|---|
| 2009/0204066 A1* | 8/2009 | Radmer | A61J 1/20 604/86 |
| 2016/0136053 A1* | 5/2016 | Weibel | B65B 3/003 141/18 |
| 2017/0065486 A1* | 3/2017 | Mosler | A61J 1/2013 |

FOREIGN PATENT DOCUMENTS

| | | |
|---|---|---|
| WO | WO 00/29049 | 5/2000 |
| WO | WO 2007/147741 | 12/2007 |
| WO | WO 2009/126720 | 10/2009 |
| WO | WO 2010/043685 | 4/2010 |
| WO | WO 2012/069401 | 5/2012 |

OTHER PUBLICATIONS

International Search Report and Written Opinion in Application No. PCT/EP2018/081553, dated Jan. 3, 2019, 12 pages.

\* cited by examiner

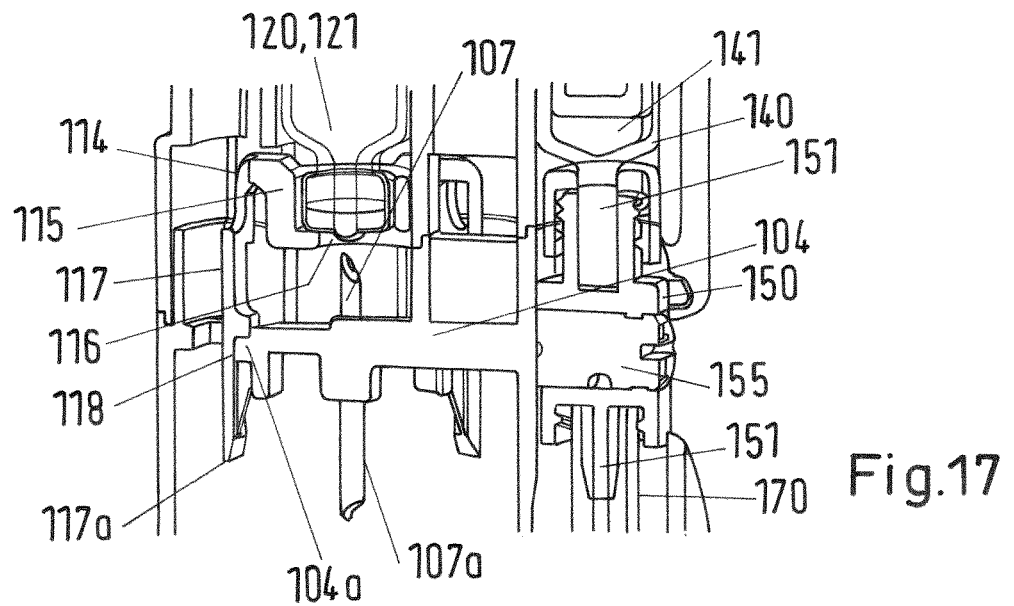
Fig.17
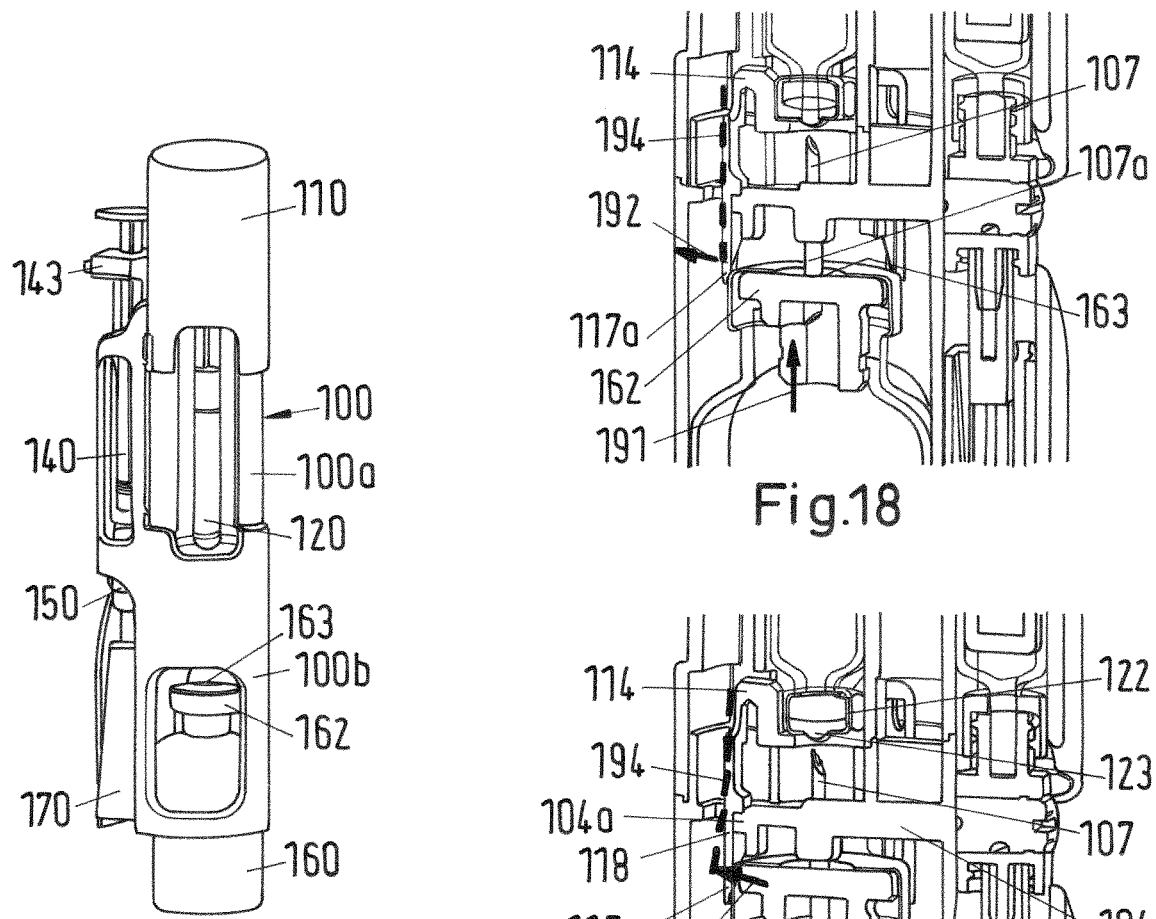
Fig.18
Fig.16
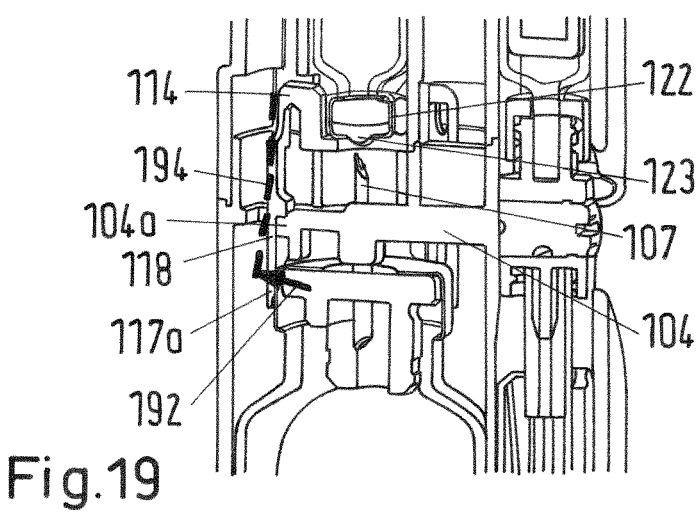
Fig.19

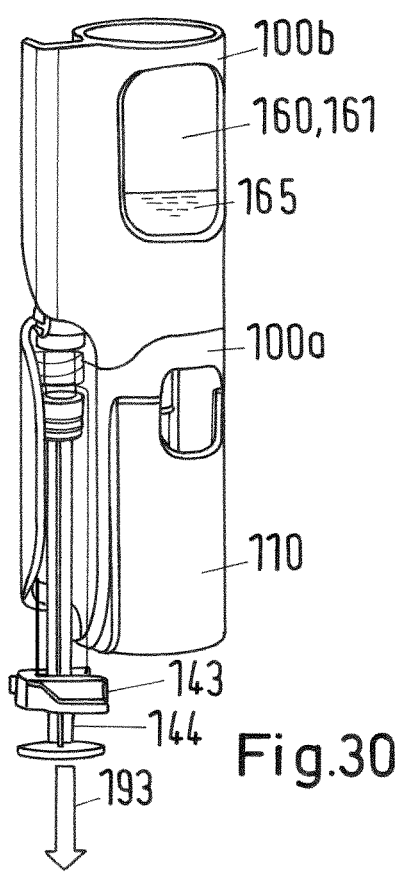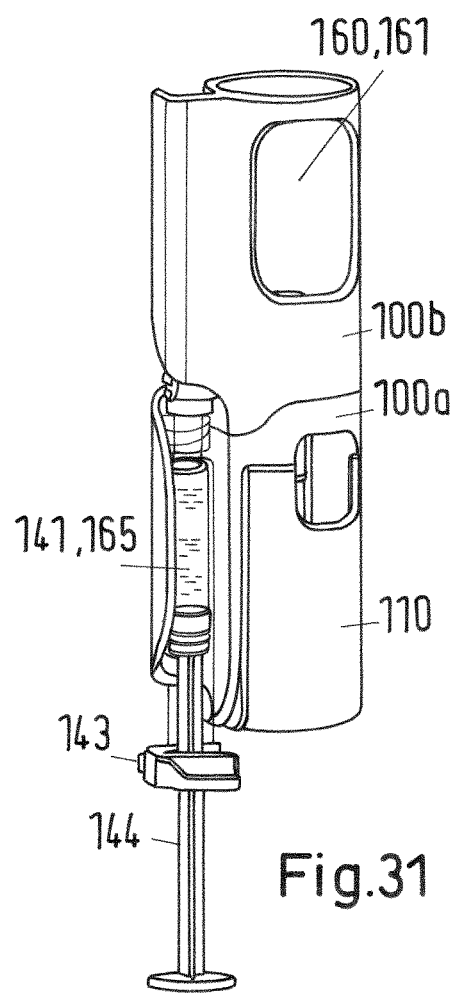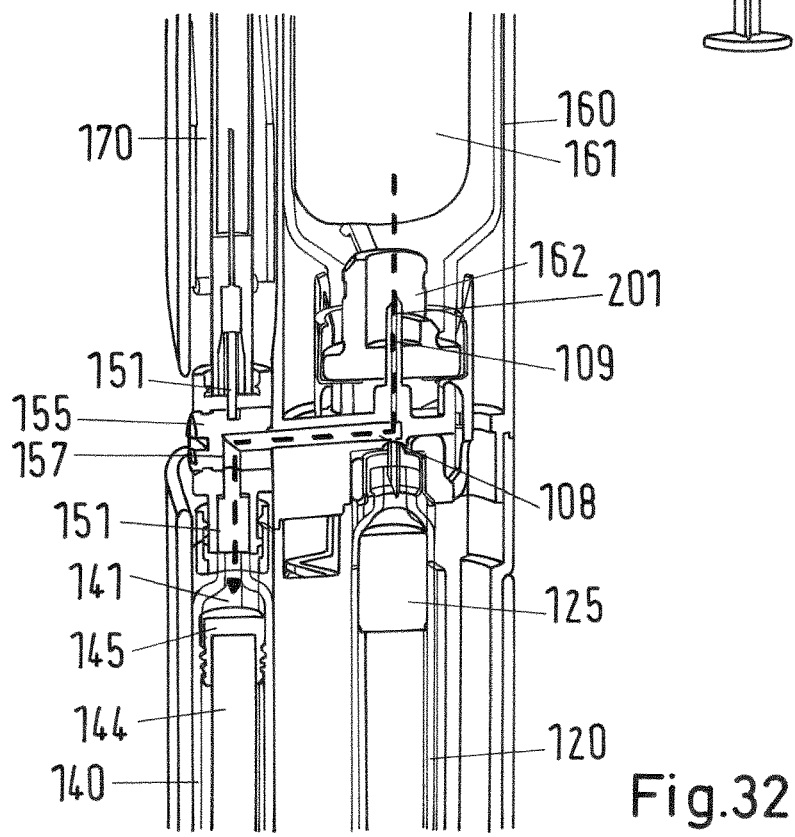

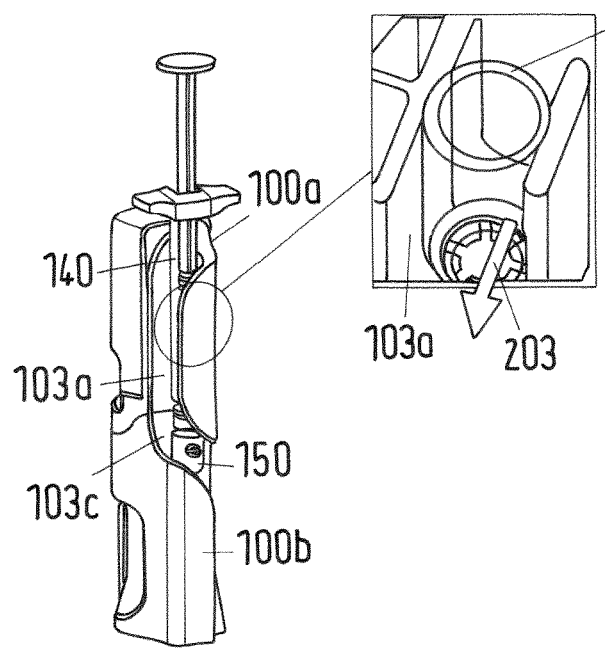
Fig.36
Fig.37
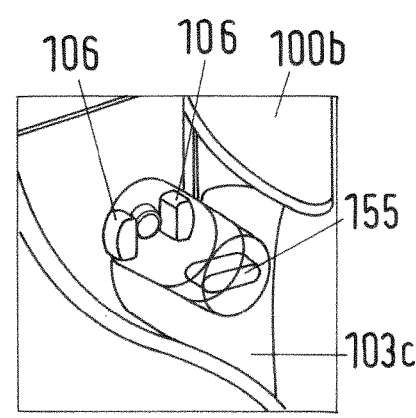
Fig.38
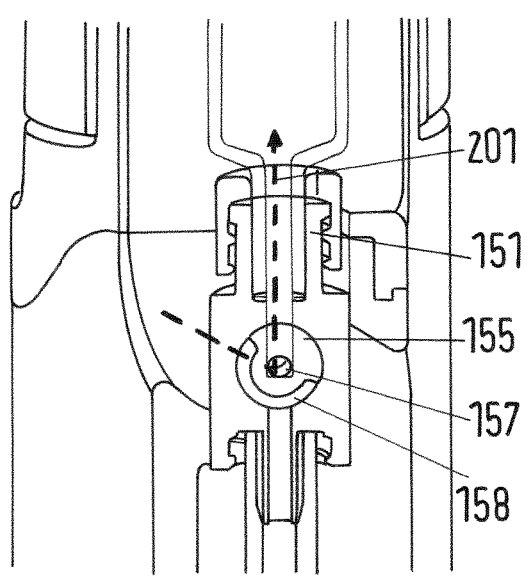
Fig.39
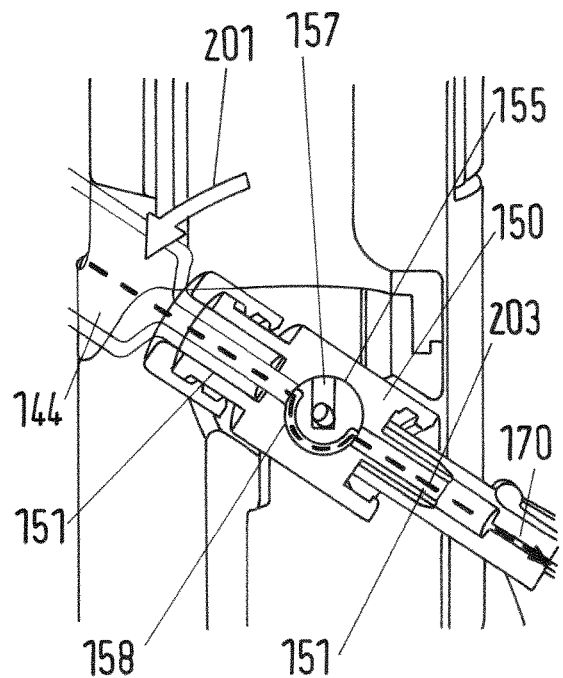
Fig.40

MIXING AND/OR RECONSTITUTION SYSTEM

CROSS REFERENCE TO RELATED APPLICATIONS

The present application is the national stage entry of International Patent Application No. PCT/EP2018/081553, filed on Nov. 16, 2018, and claims priority to Application No. EP 17306609.3, filed on Nov. 21, 2017, the disclosures of which are incorporated herein by reference.

TECHNICAL FIELD

The disclosure refers to a mixing and/or reconstitution system and a method.

BACKGROUND

Certain drugs are ideally administered in a liquid form, injected subcutaneously for the optimal therapeutic effect. However, some of these liquid drugs are unstable, having a shelf life that is relatively short. This can be a problem both for prophylactic treatments, where patients must inject themselves on a regular basis and therefore want to keep a reasonable supply of drug at home, and for emergency treatments, where patients need to keep a supply of the drug to hand but may not need it for weeks or longer.

SUMMARY

Often drugs in a concentrated liquid form or lyophilized (freeze-dried) drugs comprise separate components, namely a powder or liquid which is much more stable and has a long shelf life, and a diluent liquid. These components are typically supplied in separate vials and the user must reconstitute the drug prior to injection. Such reconstitution is often a complex process with many steps. Also, there is the risk during the reconstitution process at various points that, if the user is not careful, the drug can be contaminated.

The disclosure relates to a mixing and/or reconstitution system that comprises in particular an adaptor, an integrated injection device removably attached to the adaptor comprising a switching element, a first reservoir, containing a first material (for example pre-filled with water), wherein the first material is a fluid, and a user-operable trigger.

The adaptor further comprises a first attachment location, e.g. a recess, adapted to attach a vial, wherein the vial contains a second material within a second reservoir, wherein the second material contains a medicament formulation, a first connection element, e.g. a first needle, a flow channel providing fluid communication of the switching element and the first connection element, a sensing arrangement for detecting a pre-defined position of the vial at the first attachment location, and an interlock element which is adapted to allow operating the trigger by the user in order to establish a fluid communication between the first connection element and the first reservoir (e.g. piercing a membrane sealing the first reservoir by the first needle) only if the sensing arrangement detects the pre-defined position of the vial at the first attachment location.

In one embodiment, the first attachment location may be formed as a recess within the adaptor guiding the vial into the pre-defined position. The guiding may be further enhanced by providing a lever, for example at the end of the recess opposite from the first attachment location which guides and/or presses the vial more reliable into the pre-defined position than by the user.

In one embodiment, the interlock element may fix the first reservoir in a pre-defined position with regard to the adaptor thereby preventing operation of the trigger which is connected to the first reservoir, for example by a plunger sealing the first reservoir. If the pre-defined position of the vial is detected by the sensing arrangement the interlock element and with it the first reservoir is no longer fixed but movable, for example along the longitudinal direction of the adaptor in order to establish the fluid communication between the first connection element and the first reservoir.

In the mixing and/or reconstitution of a first material and a second material, wherein the first material is a fluid, and the second material contains a medicament formulation, where in the second material is a solid material. Reconstitution is the rehydration of a lyophilized (freeze dried) drug (e.g. medicament formulation) by a diluent (e.g. the fluid first material). The term mixing refers to any other intermixing of any first and second material.

In one embodiment, the first material is a fluid drug component and the second material is a solid drug component. In another embodiment, the second material is a fluid.

In one embodiment, the adaptor comprises an upper body (housing) and a lower body (housing) attached to each other, for example, by a snap-fit connection in order to reduce production costs.

In another embodiment the adaptor is provided with a single piece body (housing). The adaptor may have a basically cylindrical form.

In one embodiment, the trigger may be the plunger of the injection device or a plunger of a cartridge or a longitudinally movable element, e.g. a plunger, of the adaptor connected to the plunger of the cartridge. In one embodiment the plunger is movable by the user from an initial first position to a second position in which a pre-defined or the full content of the first reservoir is transferred to the vial. At the first position and/or the second position the plunger may be secured to the adaptor using a snap-fit connection. Therefore, the plunger may comprise, for example, a flexible web with a projection and the body, e.g. the upper body, a respective projection at a position of the body of the adaptor corresponding to the first and/or second position of the plunger.

In another embodiment, the first reservoir is provided by the injection device, for example in form of a syringe, or by a cartridge separate from the injection device. If the first reservoir is provided by the injection device there may be a cartridge forming the first reservoir integrated in the injection device. If the first reservoir is provided by the injection device, it is not necessary to provide a cartridge separate from the injection device for the first material.

The first connection element may be formed as a first needle or trocar.

In another embodiment, the first attachment location comprises a second connection element, e.g. a second needle or trocar or a needle section of a double-ended needle forming the connection element for the first reservoir, which is adapted to establish a fluid communication between the flow channel and the second reservoir of the vial during attachment of the vial at the first attachment location. In the pre-defined position the vial may be attached such at the first attachment location that the second connection element forms a fluid connection with the second reservoir of the vial. In this case the second connection element provides a fluid connection with the flow channel of the adaptor.

In another embodiment, the sensing arrangement is adapted to take an initial first state and a second state different from the first state and indicating that the vial is in the pre-defined position at the first attachment location.

In one embodiment, sensing arrangement may be formed in one embodiment by a flexible leg of a cartridge protector forming a latch connection with an element of the adaptor, e.g. a projection at its inner surface. In this embodiment in the initial first state the latch is locked whereas in the second state indicating that the vial is in the pre-defined position the vial, for example its cap, actuates, e.g. bends, the leg such that latch is released. In this embodiment the cartridge protector is fixed by the locked latch in the initial state. In the second state, in which the latch is released, the cartridge protector is movable along the longitudinal direction of the adaptor thereby allowing the first reservoir connected to the cartridge protector to be moved along the longitudinal direction of the adaptor in order to establish the fluid communication between the first connection element and the first reservoir.

In another embodiment, the sensing arrangement may be formed by a leg projecting from the adaptor, for example within a recess, and a slider connected to the leg. In this embodiment in the initial first state the slider is locked in a first position whereas in the second state indicating that the vial is in the pre-defined position the vial, for example its wall, actuates, e.g. bends, the leg such that slider is moved (slid) a pre-defined distance. In this embodiment the cartridge protector is fixed by the locked slider in the initial state. In the second state the opening of the slider meshes with a respective projection of the adaptor such that the slider is movable along the longitudinal direction of the adaptor thereby allowing the first reservoir connected to the slider to be moved along the longitudinal direction of the adaptor in order to establish the fluid communication between the first connection element and the first reservoir.

In a further embodiment, the first attachment location comprises at least one fixing element, e.g. a hook, for fixing the vial at the attachment position. This prevents a displacement of the vial during mixing and/or reconstitution.

In another embodiment, the trigger, e.g. the plunger of the adaptor, comprises a guard allowing access to the plunger of the injection device only if the sensing arrangement detects the pre-defined position of the vial at the first attachment location.

In a further embodiment, the first connection element may be provided at a second attachment location formed by the adaptor, for example a recess. Alternatively, the first connection element may be provided within the injection device, for example within its housing. The second attachment location realizes a precise attachment of the separate cartridge at the adaptor or an accurate fixation of the first reservoir, for example provided by a cartridge, within the injection device.

In another embodiment, the switching element is a two-way selector valve comprising an initial first channel (path) and a second channel (path), wherein the first channel provides a fluid communication between a third reservoir of the injection device and the flow channel of the adaptor and the second channel provides a fluid communication between a needle of the injection device and the third reservoir of the injection device, wherein the valve is adapted to switch between the first channel and the second channel.

Alternatively, if the first reservoir is provided by the injection device, the switching element is a two-way selector valve comprising an initial first channel (path) and a second channel (path), wherein the first channel provides a fluid communication between first connection element (provided within the injection device) and the flow channel of the adaptor and the second channel provides a fluid communication between a needle of the injection device and the first connection element and thereby the first reservoir, wherein the valve is adapted to switch between the first channel and the second channel.

In another embodiment, the switching element may be adapted to be switched between the first channel and the second channel using at least one key projecting from the surface of the adaptor, wherein the at least one key is actively connected with the switching element fixing it at the adaptor during moving and/or pivoting of the injection device relative to the adaptor. Switching between the first channel and the second channel may be realized for example by rotation of the injection device relative to the switching element, for example by an angle between 30° and 70°. In one embodiment the switching element is fixed at the housing and the injection device is rotated. Alternatively, the injection device is held fixed and the switching element is rotated, for example by the angle mentioned above.

In another embodiment, the adaptor comprises a de-aeration channel, e.g. at the second connection element. The channel may be formed as a notch at the outer surface of the connection element, which may be realized as a needle or needle section. This enables venting of the vial during filling the fluid first material into the second reservoir containing the medicament formulation. It is important that the channel has a diameter which is big enough to keep the connection open but small enough to prevent leakage of fluid from the vial.

In one embodiment, the needle of the injection device may be protected by the adaptor (caused by integration of the injection device into the adaptor) or by a needle shield and/or guard and/or or cap, for example by a folding or sliding sleeve.

In one embodiment, the injection device may be fixed at the adaptor such that the injection device's axis is oblique with regard to the axis of the cartridge and/or the vial when attached to the adaptor in order to ease operation of the injection device plunger for drawing the mixed and/or reconstituted material out of the second reservoir into the first reservoir or an injection device reservoir.

The injection device may comprise a housing, the first reservoir within an integrated volume or a cartridge or an injection device reservoir (third reservoir), and a drive mechanism for expelling the content of the mixed and/or reconstituted material out of the respective reservoir.

In one embodiment, the system comprises the vial containing a second material within a second reservoir, wherein the second material contains a medicament formulation.

A method for mixing and/or reconstitution of a first fluid material and a second material using the above described system includes attaching the vial to the first attachment location of the adaptor such that the sensing arrangement detects the vial being placed at the pre-defined position thereby allowing operation of the trigger by the user, operating the trigger by the user thereby establishing a fluid communication between the first connection element and the first reservoir (e.g. piercing a membrane sealing the first reservoir by the first needle) and emptying the first material into the second reservoir, waiting a first pre-defined time period and/or swiveling the vial a pre-defined number of times or over a second pre-defined time period, and afterwards by operation of the injection device plunger drawing the mixed and/or reconstituted material out of the second reservoir into the first reservoir or an injection device reservoir.

In one embodiment the vial is pressed to the first attachment location using a lever. The lever reduces the necessary user force needed by the user to establish a fluid communication between the first connection element and the first reservoir.

In one embodiment the method comprises the additional step that prior administration of the mixed and/or reconstituted material the injection device is detached from the adaptor and the two-way switching element is switched from the first channel to the second channel.

The term "medicament" or "medicament formulation", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound comprises at least one peptide for the treatment and/or prophylaxis of diabetes mellitus or complications associated with diabetes mellitus such as diabetic retinopathy, wherein in a further embodiment the pharmaceutically active compound comprises at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin;

human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivates are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin;

B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4(1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2,
H-Asn-(Glu)5-des Pro36, Pro37, Pro38 [Asp28] Exendin-4(1-39)-(Lys)6-NH2,
H-(Lys)6-des Pro36 [Trp(O2)25, Asp28] Exendin-4(1-39)-Lys6-NH2,
H-des Asp28 Pro36, Pro37, Pro38 [Trp(O2)25] Exendin-4(1-39)-NH2,
H-(Lys)6-des Pro36, Pro37, Pro38 [Trp(O2)25, Asp28] Exendin-4(1-39)-NH2,
H-Asn-(Glu)5-des Pro36, Pro37, Pro38 [Trp(O2)25, Asp28] Exendin-4(1-39)-NH2,
des Pro36, Pro37, Pro38 [Trp(O2)25, Asp28] Exendin-4(1-39)-(Lys)6-NH2,
H-(Lys)6-des Pro36, Pro37, Pro38 [Trp(O2)25, Asp28] Exendin-4(1-39)-(Lys)6-NH2,
H-Asn-(Glu)5-des Pro36, Pro37, Pro38 [Trp(O2)25, Asp28] Exendin-4(1-39)-(Lys)6-NH2,
H-(Lys)6-des Pro36 [Met(O)14, Asp28] Exendin-4(1-39)-Lys6-NH2,
des Met(O)14 Asp28 Pro36, Pro37, Pro38 Exendin-4(1-39)-NH2,
H-(Lys)6-des Pro36, Pro37, Pro38 [Met(O)14, Asp28] Exendin-4(1-39)-NH2,
H-Asn-(Glu)5-des Pro36, Pro37, Pro38 [Met(O)14, Asp28] Exendin-4(1-39)-NH2,
des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp (O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2) 25, Asp28] Exendin-4(S1-39)-(Lys)6-NH2, H-Asn-(Glu)5-des Pro36, Pro37, Pro38 [Met(O)14, Trp (O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two 13 sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region (CH) and the variable region (VH). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

The mixing and/or reconstitution system simplifies the reconstitution and/or mixing of a first and a second material compared to existing devices. The system supports the user in following the correct mixing and/or reconstitution sequence while minimizing the necessary operating steps preventing misuse. Additionally, usage of a high number of separate components is avoided. The adaptor with the injection device and the first reservoir, for example provided by a cartridge, is pre-assembled and may allow long-term storage, in particular if the first fluid material is water. The only separate component is formed by the vial. The interaction of the sensing arrangement and the interlock element of the adaptor may increase simplification of use and reduce misuse. The cooperation of the sensing arrangement and the interlock element makes sure that only if the vial is attached to the adaptor at the pre-defined position, (the correct position), the trigger is allowed to be operated by the user in order to establish a fluid communication between the first connection element and the first reservoir and thereby between the first reservoir containing the fluid material and the second reservoir of the vial containing the second material. After establishing this fluid communication the fluid material contained within the first reservoir is allowed to be transferred from the first reservoir to the second reservoir of the vial for mixing and/or reconstitution. Accordingly, the system provides a pre-defined sequence of steps during use. The system establishes a fluid communication between the first connection element and the first reservoir therefore, emptying the first material into the second reservoir is provided within one step by a continuous actuation of the trigger (movement into the longitudinal direction of the adaptor) once the operation of the trigger is allowed.

The system also provides large handling surfaces to hold the system and apply the necessary force for operation.

BRIEF DESCRIPTION OF FIGURES

Non-limiting, exemplary embodiments will now be described with reference to the accompanying drawings, in which:

FIG. 16 shows a perspective side view of the system of FIG. 2 during a first step of the mixing and/or reconstitution method;

FIG. 17 shows an enlarged detail of a sectional view of the system of the system of FIG. 2;

FIG. 18 shows the detail of FIG. 17 during a first step of the mixing and/or reconstitution method;

FIG. 19 shows the detail of FIG. 17 during a second step of the mixing and/or reconstitution method;

FIGS. 30-31 shows perspective side views of the system of FIG. 2 during a fifth step of the mixing and/or reconstitution method;

FIG. 32 shows a detail of a sectional view of the system of FIG. 2 during the fifth step of the mixing and/or reconstitution method;

FIG. 36 the view of FIG. 33;

FIG. 37 shows a sectional view of the system of FIG. 33 or 36;

FIGS. 38-39 show another sectional views of the system of FIG. 33 or 36;

FIG. 40 shows a sectional view of the system of FIG. 34;

DETAILED DESCRIPTION

Figure 1:
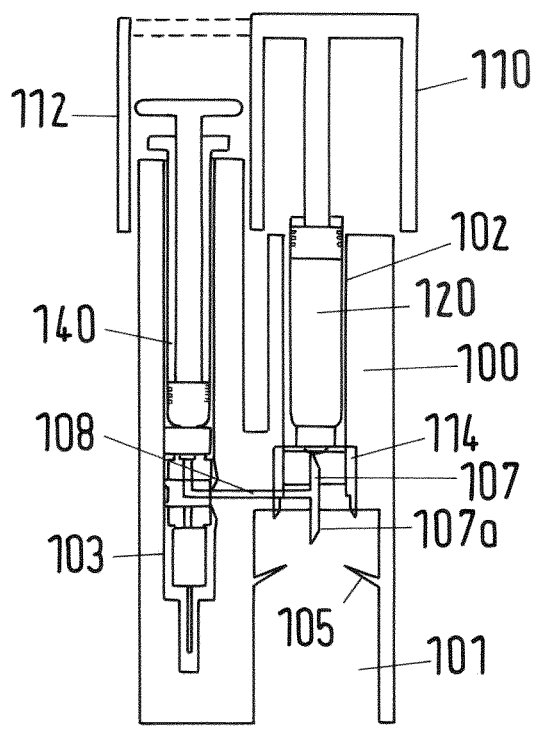
FIG. 1 shows a principle sketch of a sectional view of first embodiment of a mixing and/or reconstitution system without vial.

A first embodiment of an mixing and/or reconstitution system is shown in a concept sketch in FIG. 1 and in FIGS. 2 to 43, 59, 60, 62 and 63 also referring to the respective mixing and/or reconstitution method.

Figure 13:
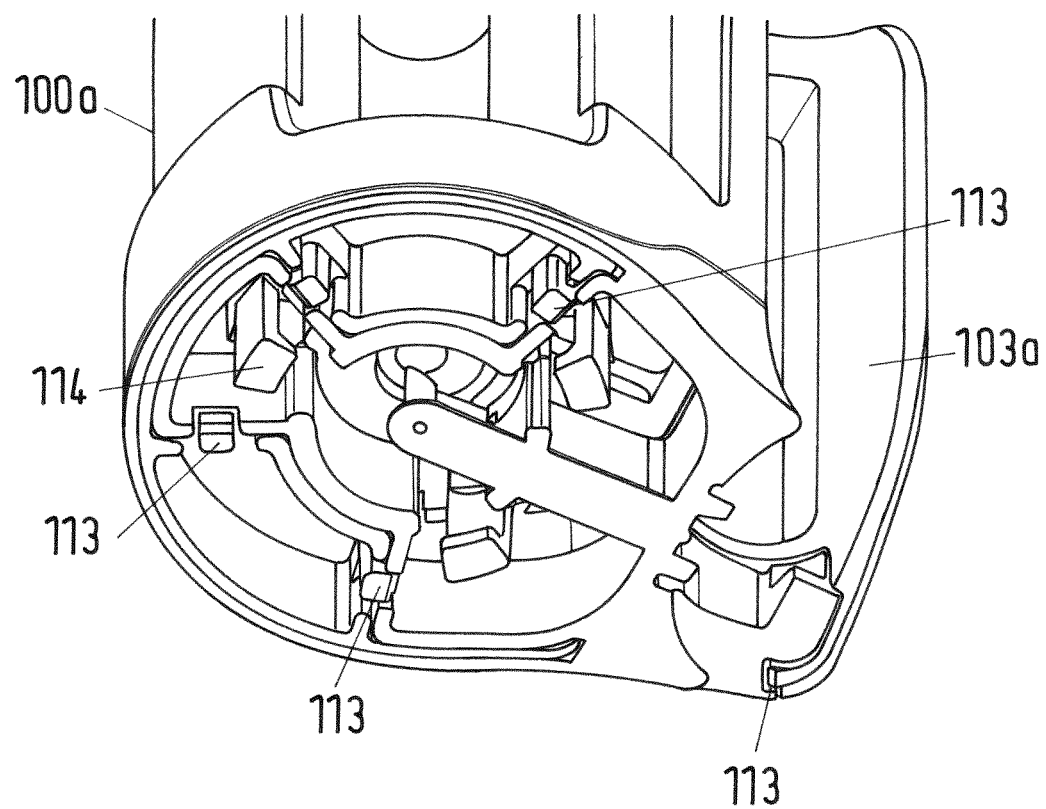
FIG. 13 shows a perspective bottom view of the upper body of the system of FIG. 2.
Figure 14:
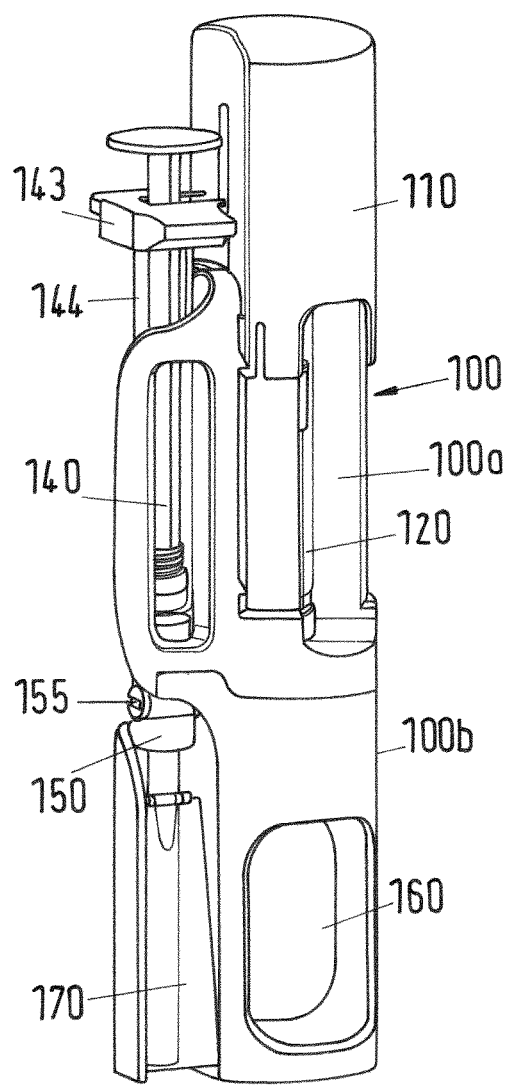
FIG. 14 shows another perspective side view of system of FIG. 2 with vial.
Figure 15:
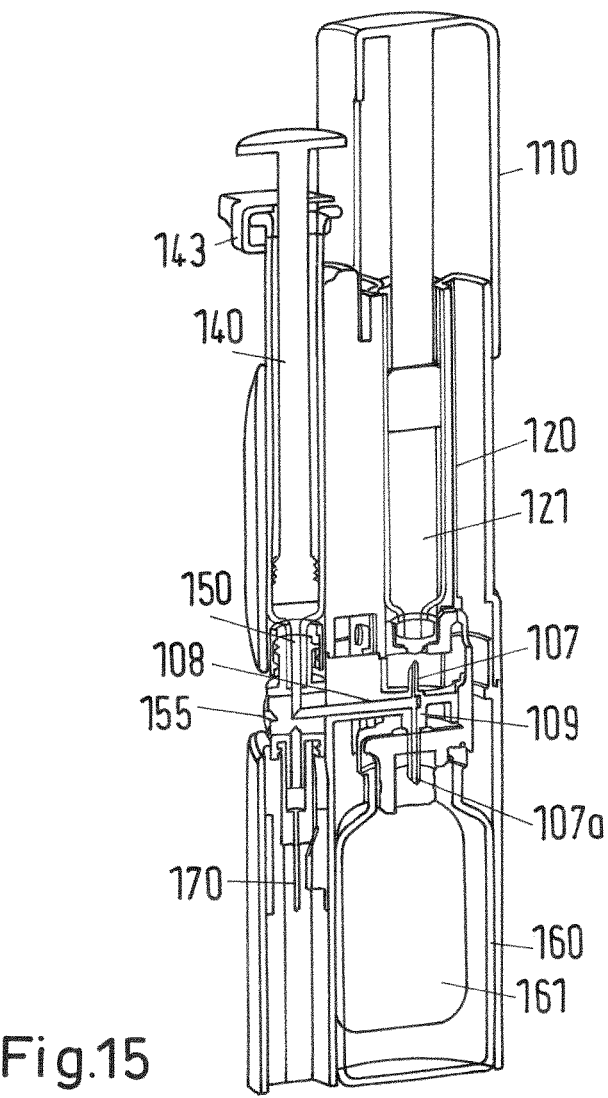
FIG. 15 shows a sectional view of the system of FIG. 2 with vial.

The system comprises an adaptor 100 with a first recess 101 for a vial 160, a cartridge 120 accommodated within a second recess 102 of the adaptor 100 and an injection device in form of a syringe 140 accommodated within a third recess 103 of the adaptor 100. Further, the adaptor 100 may be formed as a single-piece as shown in FIG. 1 or, alternatively, may comprise an upper body 100a and a lower body 100b as depicted in FIGS. 2 to 43. The upper and lower bodies 100a, 100b may be fixed together by a snap-fit connection 130 which is shown in FIG. 13.

The syringe 140 may be an empty 3 ml syringe and the cartridge 120 may be a 3 ml cartridge pre-filled with 2 ml water. As a vial 160 a standard 20 ml vial may be used.

Figure 2:
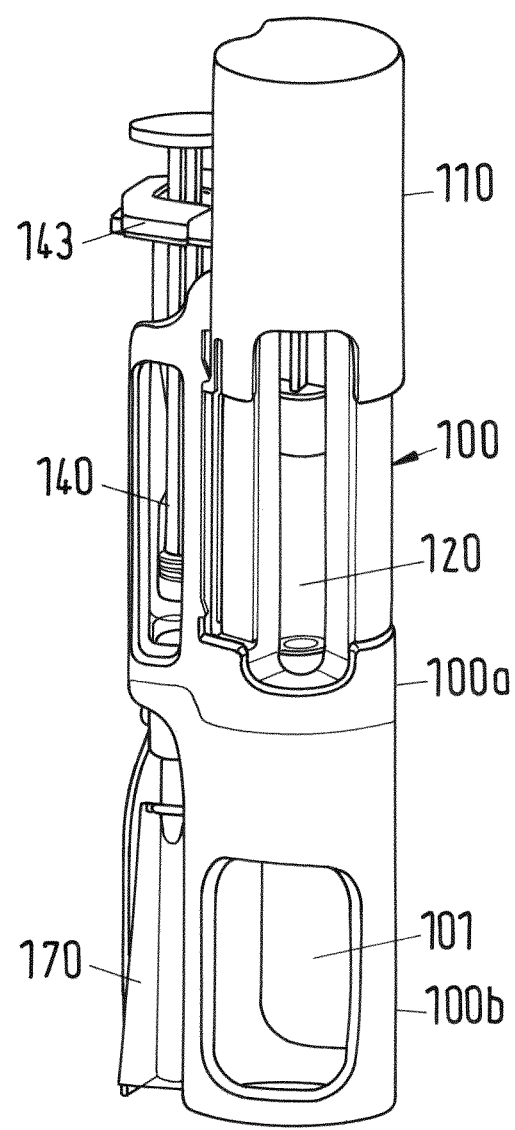
FIG. 2 shows a perspective side view of the first embodiment of a mixing and/or reconstitution system in an initial state without vial.
Figure 3:
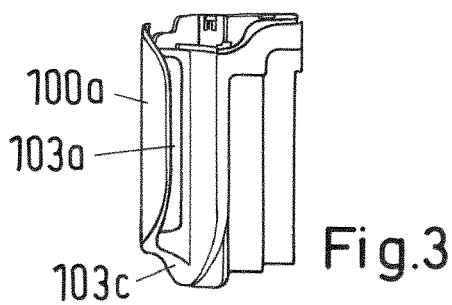
FIG. 3 shows a perspective side view of an upper body of the system of FIG. 2.
Figure 4:
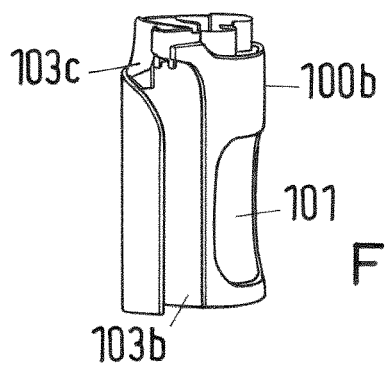
FIG. 4 shows a perspective side view of a lower body of the system of FIG. 2.
Figure 5:
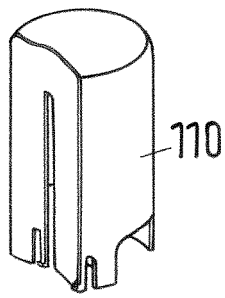
FIG. 5 shows a perspective side view of a plunger of the system of FIG. 2.

The adaptor 100 is an elongated, basically cylindrical component which may be placed with its lower end surface on a desk such that its longitudinal direction runs perpendicular to the desk surface. The first and second cylindrical recesses 101, 102 are accommodated one above the other along a longitudinal direction, wherein the first recess 101 may be accommodated below the second recess 102 as shown in FIGS. 1 and 2, for example. The third cylindrical recess 103 for the syringe 140 is located in parallel to the first and second recesses 101, 102.

The cylindrical recess 101 for the vial 160 may comprise one or more hooks 105 in order to fix the vial 160 when it is accommodated within the recess 101. Each hook 105 may be formed as a projection slanting slightly in the upper direction in order to obstruct the vial from dropping out of the first recess 101.

On the upper end of the first recess a double-ended needle or trocar 107 is provided within a horizontal rib 104 of the lower body 100b. The lower end 107a projects into the first recess 101 from above, whereas the upper end of the double-ended needle 107 projects into the second recess 102 from underneath. The vertical flow channel 109 of the double-ended needle 107 is connected with a horizontal flow channel 108 running within the horizontal rib 104 of the lower body 100b (see e.g. FIG. 15).

The second recess 102 comprises the cylindrical cartridge 120 which contains the cartridge reservoir 121. The cartridge reservoir 121 is closed at its lower end by a cap 122 comprising a membrane 123 (see FIG. 11, for example). At the upper end the cartridge reservoir 121 is closed by a plug 125. The cartridge 120 contains within its reservoir 121 a first fluid material for mixture and/or reconstitution with the second material provided by the vial. The cartridge 120 is slidably fixed within the second recess 102. In an initial state the cartridge 120 is accommodated such within the second recess 102 that an interlock element in form of a cartridge protector 114 keeps the lower end of the cartridge 120 with the membrane 123 in a certain distance from the upper end of the needle 107 so that the needle 107 cannot pierce the membrane 123.

Figure 6:
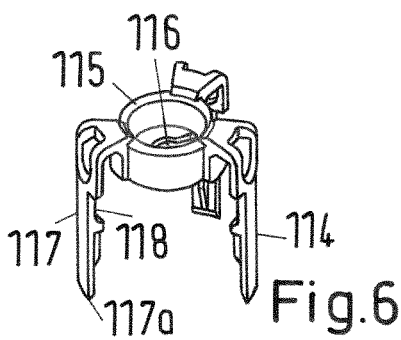
FIG. 6 shows a perspective side view of a cartridge protector of the system of FIG. 2.

The cartridge protector 114, which is shown in detail in FIG. 6, comprises a central flange 115 which receives the lower end of the cartridge 120, in particular its cap 122. This is shown in detail for example in FIG. 17. In the center of the flange 115 an opening 116 is provided so that the needle 107 may pierce the membrane 123 when the cartridge protector 114 is moved into the direction of the needle. The cartridge protector 114 further comprises for example three legs 117 projecting from the flange 115, wherein each leg has a front end (lower end) 117a. Additionally, each leg 117 comprises at its inner surface a recess 118 with an upper edge 118a which are engaged with respective projections 104a of the horizontal rib 104 of the lower body 100b in an initial state (see also FIG. 59). In the initial state the cartridge protector 114 supports the cartridge 120 at a pre-defined distance from the upper end of the needle 107 as indicated above. The legs 117 of the cartridge protector 114 point into downward direction and are slightly flexible with regard to a transversal force. They are provided such within the lower body 100b of the adaptor 100 that their front ends 117a project into the first recess 101.

Figure 22:
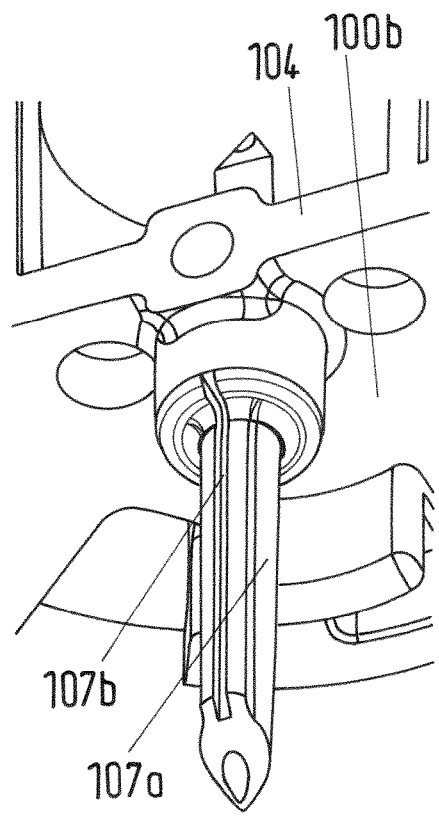
FIG. 22 shows an enlarged detail of a sectional view of the lower body of the system of FIG. 2.
Figure 23:
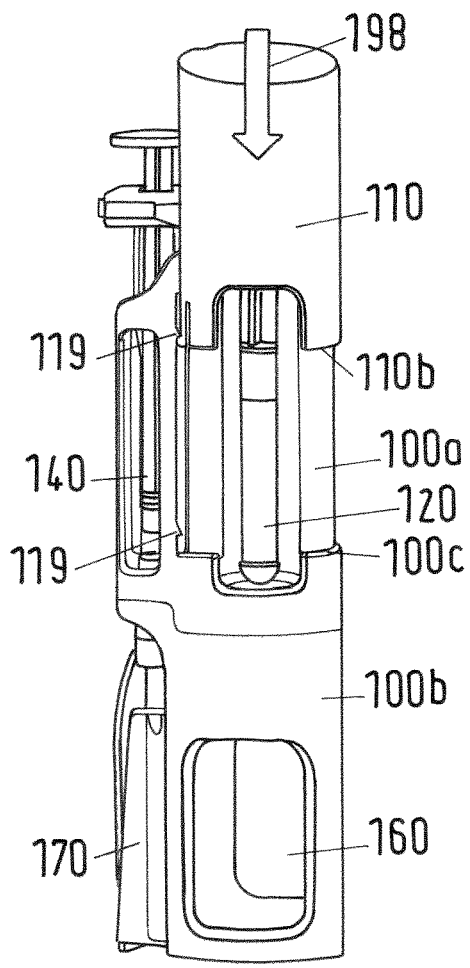
FIG. 23 shows a perspective side view of the system of FIG. 2 during the third step of the mixing and/or reconstitution method depicted in FIGS. 20 and 21.
Figure 24:
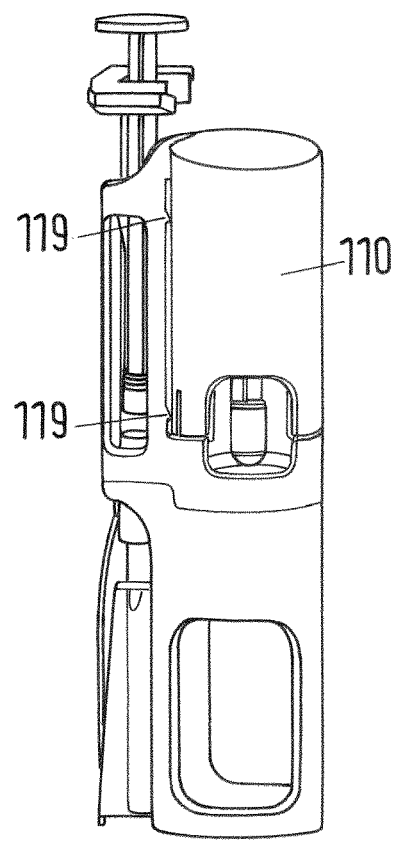
FIG. 24 shows a perspective side view of the system of FIG. 2 at the end of the third step of the mixing and/or reconstitution method.

At the upper end of the upper body 100a of the adaptor 100 there is a trigger in form of a plunger 110 which is slidable along the outer surface of the upper body 100a (FIGS. 2 to 43) or of the adaptor 100 (FIG. 1) between an initial first position shown in FIG. 23 and a second end position shown in FIG. 24. In the second position the lower end face 110b of the plunger 110 arrives at the stop surface 100c of the upper body 100b of the adaptor 100 (see FIG. 25). The plunger 110 is basically formed as a hollow cylinder closed at its upper end that caps the second recess 102 of the adaptor 100 containing the cartridge 120. The plunger further comprises a cylindrical rod 110c projecting from the inner surface of the upper end downwards as shown in FIG. 26. The lower end face of the rod 110c abuts on the plug 125 of the cartridge 120.

Figure 25:
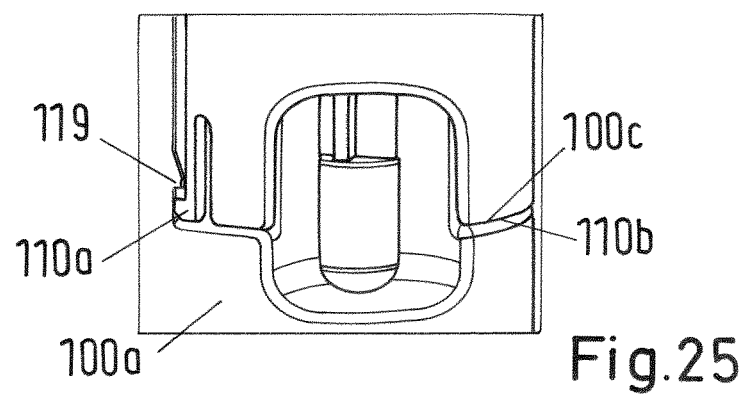
FIG. 25 a detail of FIG. 24.
Figure 26:
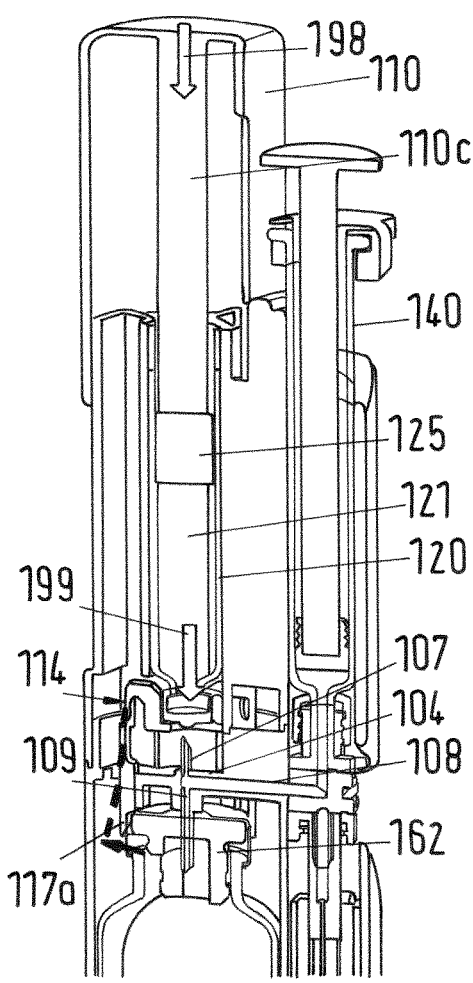
FIGS. 26-28 details of a sectional view of the system of FIG. 2 during the third step of the mixing and/or reconstitution method.

As shown in FIG. 25 the lower portion of the shell of the plunger 110 further comprises a flexible web 110a with a tangential projection. The web 110a meshes with projections 119 of the upper body 100a accommodated along the longitudinal direction of the adaptor forming together two snap-fit connections in a first initial position shown in FIG. 23 and in a second end position of the plunger 110 shown in FIGS. 24 and 25.

In the embodiment shown in FIG. 1 the plunger 110 further comprises a guard 112 covering and thereby protecting the upper end of the syringe 140 in the initial position of the plunger 110.

Figure 10:
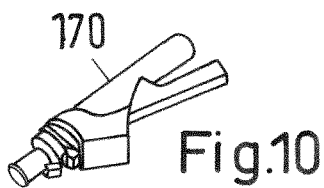
FIG. 10 shows a perspective side view of a needle with protection element of the system of FIG. 2.
Figure 11:
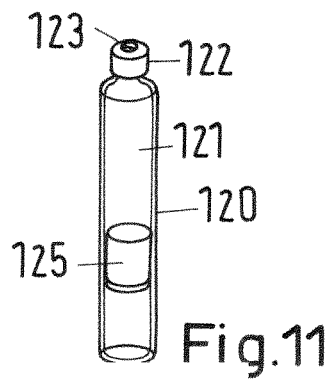
FIG. 11 shows a perspective side view of a cartridge of the system of FIG. 2.
Figure 12:
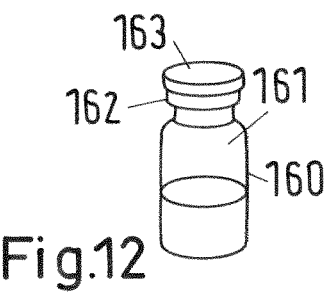
FIG. 12 shows a perspective side view of a vial used for the system of FIG. 2.
Figure 20:
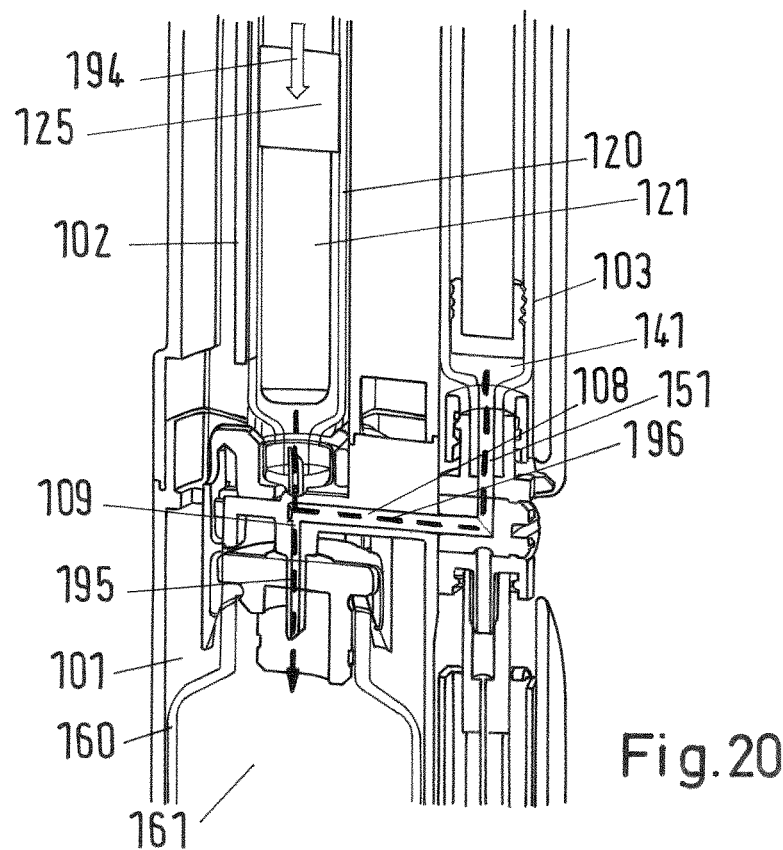
FIG. 20 shows an enlarged detail of a sectional view of the system of the system of FIG. 2 during a third step of the mixing and/or reconstitution method.

The syringe 140 accommodated within the third recess 103 of the adaptor 100 comprises a syringe reservoir 141, a handle 143 and a plunger 144. In the initial position the plug 145 fixed at the lower end of the plunger 144 is in its lowest position so that the volume of the syringe reservoir 141 is almost zero as shown in FIG. 1 or 20, for example. In the initial state the syringe reservoir 141 is empty. The syringe 140 further comprises an attachment element 150 containing a two-way selector valve 155 as a switching element at the lower end of the syringe reservoir 141. The syringe further comprises a needle 170 with protection element as shown in FIGS. 2 and 10, for example. Alternatively, the needle may be integrated within and protected by the adaptor 100 body as shown in FIG. 1. The needle 170 is attached to the attachment element 150.

Figure 7:
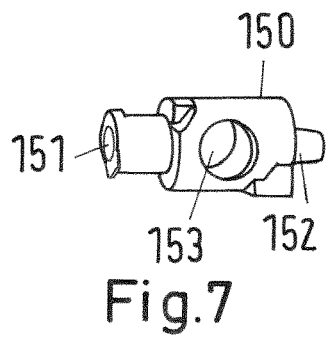
FIG. 7 shows a perspective side view of an attachment element of the system of FIG. 2.

The attachment element 150 is formed as a basically cylindrical element and is shown in detail in FIG. 7. The attachment element 150 comprises a through-going cylindrical channel 151 extending along the longitudinal direction of the attachment element 150 from the upper to the lower end of the attachment element 150. The central portion of the attachment element 150 is formed by a vertical opening 153 accommodating the valve 155. The axis of the cylindrical opening 153 runs perpendicular to the axis of the channel 151. The attachment element 150 further comprises an attachment section 152 at its lower end at which the needle 170 may be fixed. At its upper end the attachment element 150 is connected to the syringe reservoir 141 as shown, for example, in FIG. 20. From this FIG. it can be derived that the upper section of the flow channel 151 is connected to the syringe reservoir 141 forming a fluid connection.

Figure 8:
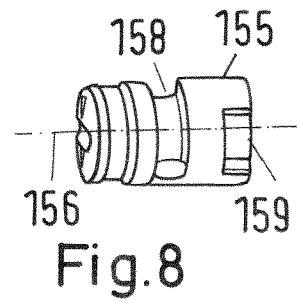
FIG. 8 shows a perspective side view of a valve of the system of FIG. 2.
Figure 9:
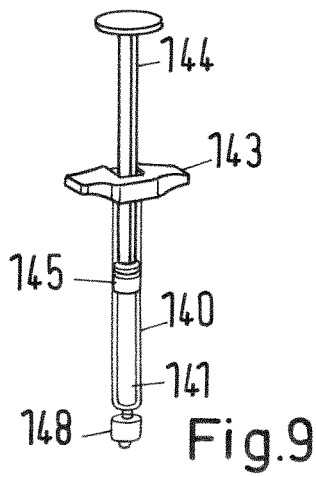
FIG. 9 shows a perspective side view of a syringe of the system of FIG. 2.

The valve 155 is formed by a cylindrical element with a longitudinal axis 156 and comprises a first channel 157 and a second channel 158 (see FIGS. 8, 39 and 40).

Figure 62:
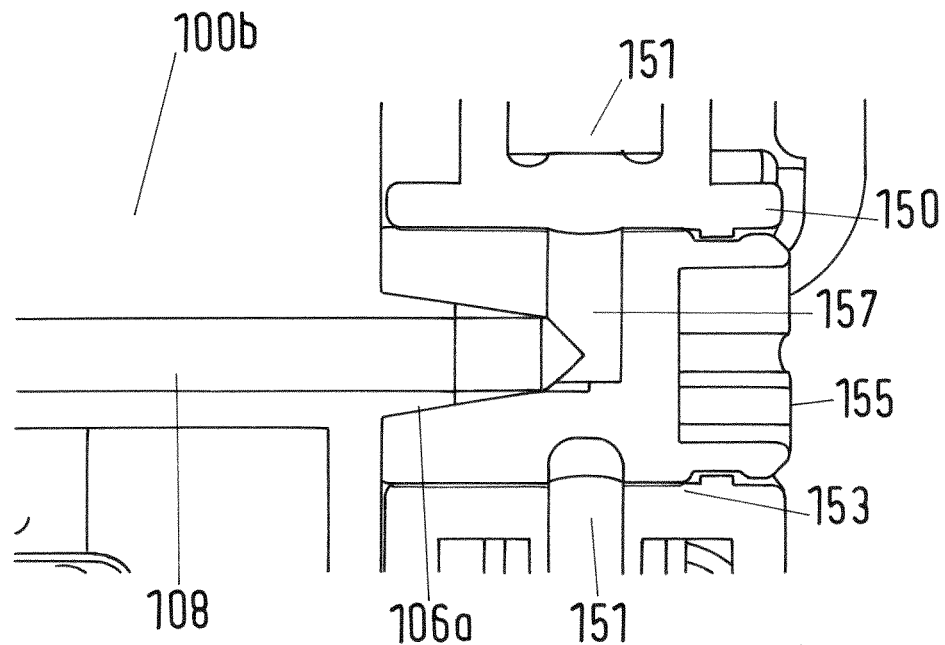
FIG. 62 shows a sectional view of the valve of the system of FIG. 2 in detail.

The two-way selector valve 155 is pivotable accommodated within the vertical opening 153 of the attachment element 150. The valve 155 may be rotated with respect to the attachment element 150 by rotation of the syringe 140, for example by an angle between 30° and 70°. This is facilitated by two elongated projections 106 and one conical projection 106a shown in FIG. 63 which mesh with respective recesses of the valve 155 as shown in FIGS. 8 and 62. As one can derive from FIG. 8 a recess 159 at the outer surface of the attachment element 155 cooperate with the elongated recess 106 of the lower body 100b. Further, as depicted in FIG. 62, the conical projection 106a meshes with a respective central and conical recess of the valve. This projection 106a further forms the connection of a first channel 157 of the valve with the horizontal channel 108 of the adaptor 100. The first channel 157 is an angled channel (e.g. angle 90°) which in an initial state of the adaptor 100 forms a fluid connection between the upper section of the channel 151 of the attachment element 150 (and thereby the syringe reservoir 141) and the horizontal channel 108 of the adaptor 100 as best shown in FIG. 62. The second channel 158 of the valve 155 (depicted for example in FIGS. 8 and 40) forms a fluid connection between the upper section of the channel 151 (and thereby the syringe reservoir 141) and the lower section of the channel 151 of the attachment element 150 (and thereby the needle 107 attached to the attachment element 150) when the valve 155 is switched to a rotated position. The rotation (switch) of the valve 155 relative to the attachment element 150 is explained in detail below.

The system further comprises a vial 160 which has the form of a bottle and contains a vial reservoir 161 which is closed on one end by the vial body and sealed on the other end by a cap 162 with a membrane 163. The vial 160 is depicted in detail in FIG. 12, for example. In an initial state the vial 160 is separate from the adaptor 100 at which the cartridge 120 is fixed within the second recess 102 and the syringe 140 within the third recess 103. The vial 160 may be stored separately from the adaptor 100 with syringe 140 and cartridge 120. The vial contains in its reservoir 161 a second material with a medicament formulation which is to be mixed and/or reconstituted with the first material contained within the cartridge reservoir 121.

The needle 170 may comprise a protection element as depicted in FIG. 10 and attached to the attachment section 152 of the attachment element 150 of the syringe 140. It comprises a needle cap protecting the needle so that user injury is prevented prior and after injection. The needle cap may be removed or pulled off prior administration of a mixed and/or reconstituted material 165 contained in the syringe reservoir 141 after mixing and/or reconstitution using the system.

In the following the mixing and/or reconstitution method is explained in detail with regard to the first embodiment. For the mixing and/or reconstitution the pre-fixed system as shown in FIG. 2 in its initial state is used (comprising the adaptor 100, the cartridge 120 and the syringe 140) together with the vial 160 (see FIG. 12). As indicated above the cartridge 120 comprises the fluid component for mixing and/or reconstitution, whereas the vial 160 comprises the solid or lyophilized component.

The system provides a highly user friendly operation which is also very safe with regard to unintentional misuse. The system is constructed such that the vial may be stored separately from the system comprising the adaptor 100, the cartridge 120 and the syringe 140.

In the first step the vial 160 is inserted into the first recess 101 as shown in FIG. 16. At the end of the insertion the cap 162 with the membrane 163 of the vial 160 is pressed against the lower end 107a of the double-ended needle 107 as indicated by arrow 191 in FIG. 18 so that the membrane 163 is pierced by this needle end 107a until the cap 162 reaches respective stop surfaces at the rib 104 of the lower body 100b (see FIGS. 18 and 19).

At the same time detecting a pre-defined (correct) position of the vial 160 (in which the membrane 163 of the vial is fully pierced by the lower end 107a of the needle 170) by the sensing arrangement comprising the cartridge protector 114 and the lower body 100b, particularly its rib 104, the lower ends 170a of the cartridge protector 114 are bent sideways by the cap 162 of the vial 160 as indicated by arrow 192 and dashed line 194 in FIGS. 18 and 19. The bending of the legs 117 is because the cap 162 has a slightly bigger cross section than the inner distance of the legs 117. As soon as the lower end 117a of each leg 117 is bent to the side (see the dashed line 194 in FIGS. 18 and 19) by a sufficient amount the recess 118 and edge 118a de-latch from the engagement with the projection 104a of the rib 104 of the lower body 100b. Due to the de-engagement of the cartridge protector 114 from the adaptor 100 lower body 100b the cartridge protector 114 is no longer fixed to and supported by the adaptor 100 but allowed to slide into longitudinal direction, particularly downwards. In other words, the amount of bending of the cartridge protector 114 legs 117 indicates the pre-defined correct position of the vial 160 after insertion of the vial 160 into the first recess 101. In case the position of the vial 160 does not correspond to the pre-defined position the operation of the trigger (plunger 110) is prevented (or locked) by the interlock element (cartridge protector 114) as the cartridge 120 cannot move due to the firm support of interlock element (cartridge protector 114) by the adaptor 100. As soon as the pre-defined position of the vial 160 is reached after insertion into the first recess 101, the now de-latched and slidable interlock element (cartridge protector 114) allows operating of the trigger (plunger 110).

In a third step, as soon as the vial is in the pre-defined position, the user presses the trigger (plunger 110) downwards as shown in FIG. 20 by arrow 194 or in FIG. 23 or 26 by arrow 198. Thereby, the plunger 110 slides from its initial position shown in FIG. 23 to its end position shown in FIG. 24. The user needs to press the plunger 110 with such a force that the flexible web 110a comes out of engagement with and overrides the projection 119 as shown in FIG. 23. In the end position of the plunger 110 the second projection 119 at a lower end of the upper body 100a catches into place as shown in FIGS. 24 and 25 engaging the web 110a and preventing retraction of the plunger 110. Further, in the second end position, the lower end face 110b of plunger 110 arrives at a respective stop surface 100c of the upper body 100b.

Figure 27:
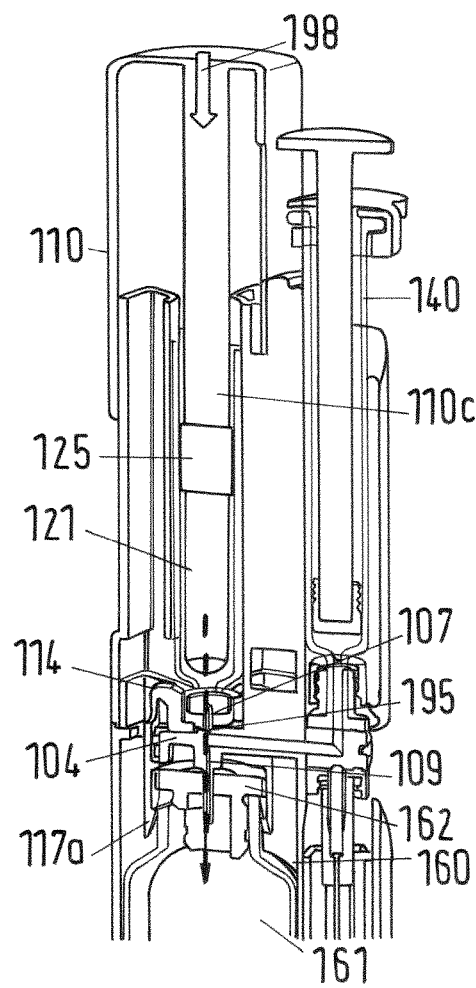

With the downward movement of the plunger 110 the rod 110c of the plunger is pulled down driving the now slidable and no longer locked cartridge 120 into downward direction as indicated by arrow 191 in FIGS. 26 and 27. As soon as the cap 122 of the cartridge 120 reaches the upper end of the double-ended needle 107 the needle 107 pierces the membrane 123 so that a fluid connection is established between the cartridge reservoir 121 and the vertical channel 109 of the double-ended needle 107 and thereby the horizontal channel 108 as well. The end position of the cartridge 120 within the second recess 102 where the lower surface of the flange 115 of the cartridge protector 114 abuts the upper surface of rib 104 is shown in FIG. 27.

When the plunger 110 is further pushed down by the user as shown in FIG. 20 by arrow 194 or in FIG. 27 by arrow 198 the first fluid material contained within the cartridge reservoir 121 is driven by the plunger 125 into the vial reservoir 161 through the vertical flow channel 109 of the double-ended needle 107. This is depicted in FIGS. 20 and 27 by arrow 195. Due to the inner pressure within the horizontal flow channel 108 or the adjacent channels 157 of the valve 155 and 151 of the attachment element 150 the first material is driven to the vial 160 only. This is depicted by the dashed line 196 in FIGS. 20 and 21. Because the membrane 163 of the vial 160 is pierced prior the membrane 123 of the cartridge 120 the vacuum in the vial reservoir 161 is equalized. Further, the cartridge protector 114 ensures that only if the vial 160 is in the correct position the cartridge 120 may be pierced and cartridge reservoir 121 may be emptied. This ensures correct operation of the system.

Figure 21:
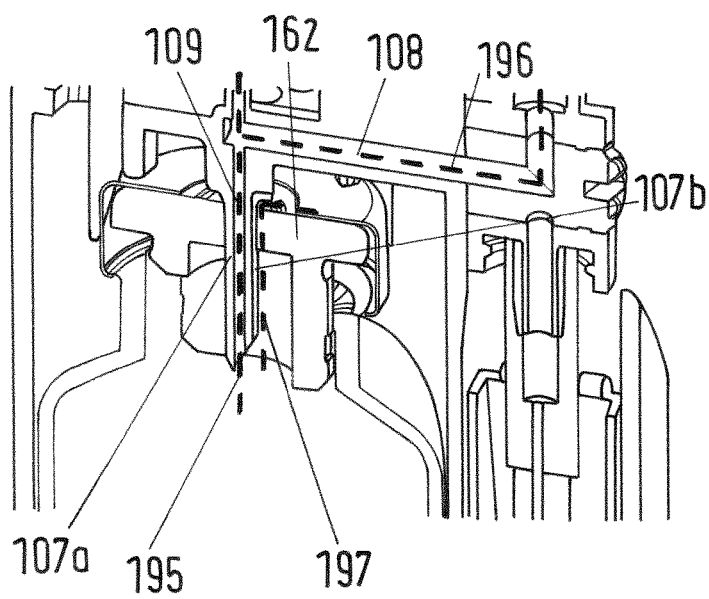
FIG. 21 shows an enlarged detail of FIG. 20.

After piercing of the cartridge all three components (i.e. the cartridge 120, the vial 160 and the syringe 140) are connected by the flow channel composed of the flow channel 151 of the attachment element 150, the horizontal flow channel 108 and the vertical flow channel 109 of the double-ended needle. Emptying of the cartridge 120 creates an excess pressure within the vial (if not vented) which may move the syringe 140 or the bung 125 of the cartridge 120 (in one embodiment the cartridge 120 cannot be moved when the plunger 110 is locked in the second end position). In order to prevent excess pressure within the vial reservoir 161 the double-ended needle 107 comprises a de-aeration notch 107b at the outer surface of its lower end 107a which is depicted in FIGS. 21 and 22. The excess air within the vial reservoir 161 leaves the vial reservoir 161 along the de-aeration notch 107b as depicted in FIG. 21 by the dashed line 197. For correct operation the notch 107b shall have a diameter which is big enough to keep the membrane 163 of the vial 160 open but small enough to prevent leakage of liquid from the vial reservoir 161.

Figure 28:
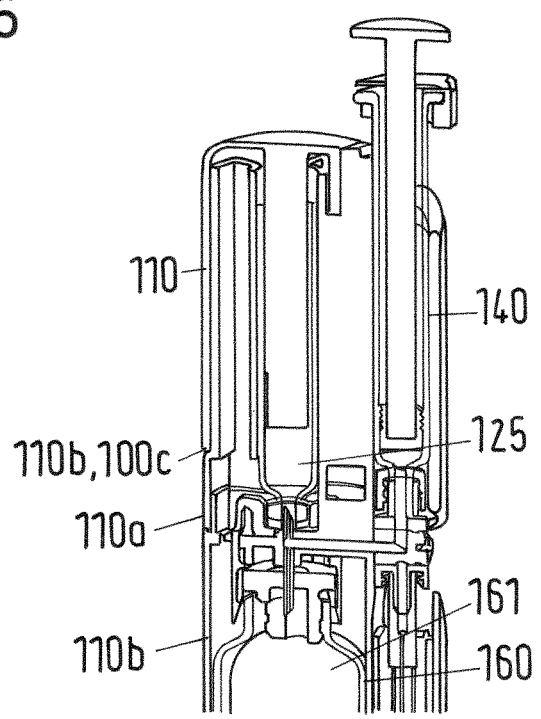

The user presses the plunger 110 as long as the cartridge reservoir 121 is fully emptied into the vial 160 and the end position of the plunger 110 is reached as shown in FIGS. 24, 25 and 28.

Figure 29:
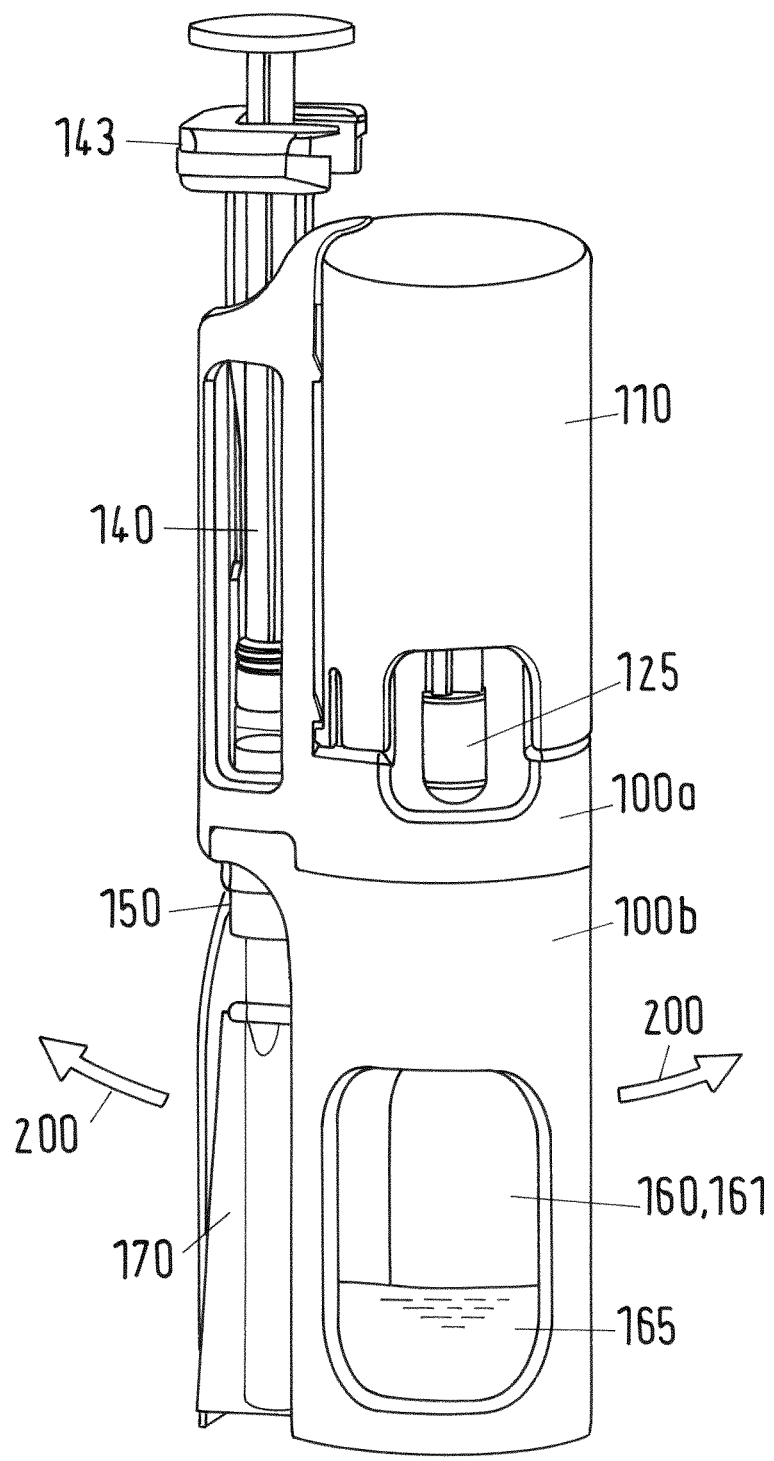
FIG. 29 shows a perspective side view of the system of FIG. 2 during a fourth step of the mixing and/or reconstitution method.

In the next step, in order to fully mix and/or reconstitute the first and the second material contained within the vial reservoir 161 the system is swiveled or pivoted back and forth as shown by arrows 200 in FIG. 29 over a pre-defined time period. The fully mixed and/or reconstituted material is depicted with reference number 165. In one embodiment, the content of the vial reservoir 161 is visible through to large windows in the lower body 100b of the adaptor 100 so that the user may observe the correct mixing and/or reconstitution process.

In the next step the system may be reversed as shown in FIG. 30. However, alternatively, the reversal is not mandatory. In this step, the plunger 144 of the syringe 140 is pulled as shown by arrow 193 in FIG. 30 such that the mixed and/or reconstituted material 165 contained within the vial reservoir 161 is drawn into the syringe reservoir 141. The mixed and/or reconstituted material 165 flows along the channel 109 of the double-ended needle 107, the horizontal channel 108, the first channel 157 of the valve 155 and the upper section of the channel 151 of the attachment element 150 (in the reverse position of the system shown in FIGS. 30 to 32 this section appears to be the lower section of the channel 151) as depicted in FIG. 32 by arrow 201. The end position of the system of this step is shown in FIG. 31. In the end position the whole mixed and/or reconstituted material 165 is contained within the syringe reservoir 141.

Figure 33:
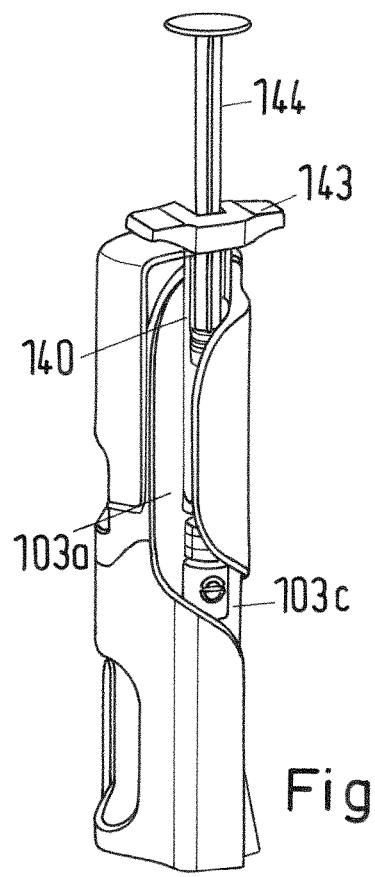
FIGS. 33-34 shows perspective side views of the system of FIG. 2 during a sixth step of the mixing and/or reconstitution method.
Figure 34:
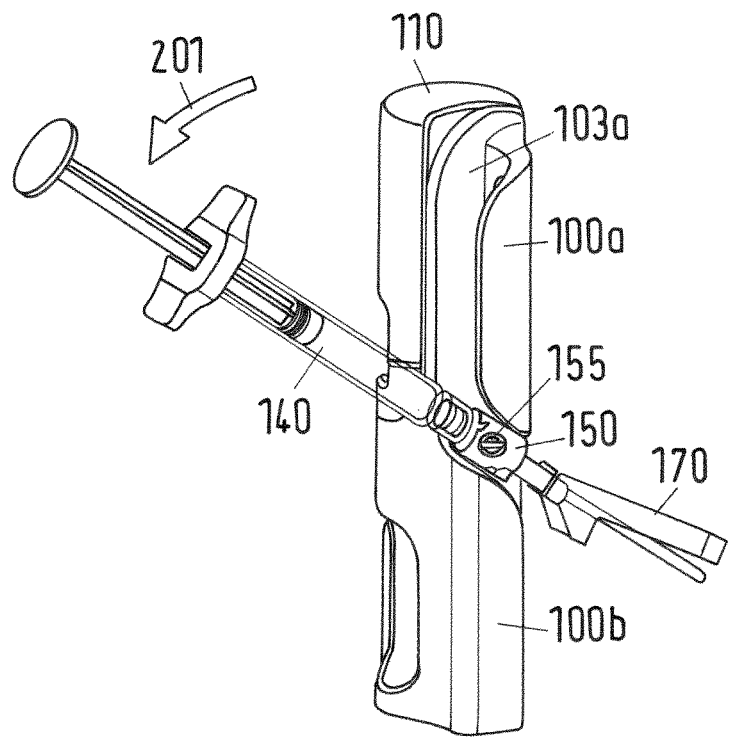
Figure 63:
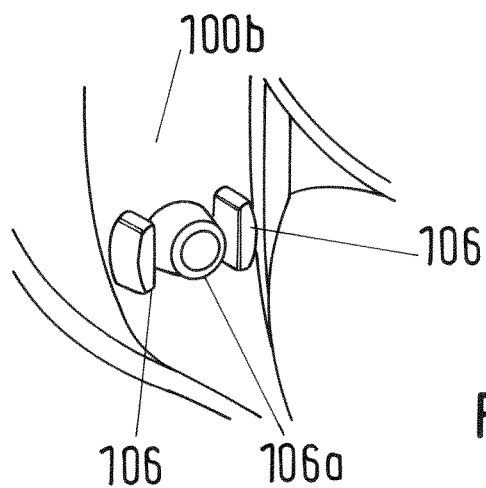
FIG. 63 shows a perspective side view of the lower body of the system of FIG. 3 in detail.

In the following step, the system may be reversed again as shown in FIG. 33. Further, the syringe 140 is turned around a horizontal axis corresponding to the longitudinal axis 156 of the valve 155 (see FIG. 8) as shown in FIG. 34 by arrow 201. In this step the upper portion of the syringe 140 comprising the syringe reservoir 141 is detached from the third recess 103a within the upper body 100a and the lower portion of the syringe 140 comprising the needle 170 from the third recess 103b within the lower body 100b. Further, the valve 155 is kept fixed at the lower body 100b of the adaptor 100 and the syringe 140 and with it the attachment element 150 are rotated such that there is a relative rotation of the valve 155 and the attachment element 150 causing that the first channel 157 of the valve 155 is closed and that the second channel 158 is opened as indicated in FIGS. 39 and 40. The mechanical fixation of the valve 155 is provided by the elongated projections 106 at the intermediate portion 103c of the third recess 103 at the lower housing 100b as shown in FIGS. 38 and 63 which cooperate with the recesses 159 of the valve 155 (see FIG. 8). In the pivoted position of the valve 155 relative to the attachment element 150 there is a fluid connection between the syringe reservoir 141 and the needle through the second channel 158 of the valve 155 as depicted in FIG. 40 by arrow 203. This allows the administration of the mixed and/or reconstituted material 165 accommodated within the syringe reservoir 141 by needle 170. The mixing and/or reconstitution method is thereby finished and the syringe is ready to use.

Figure 35:
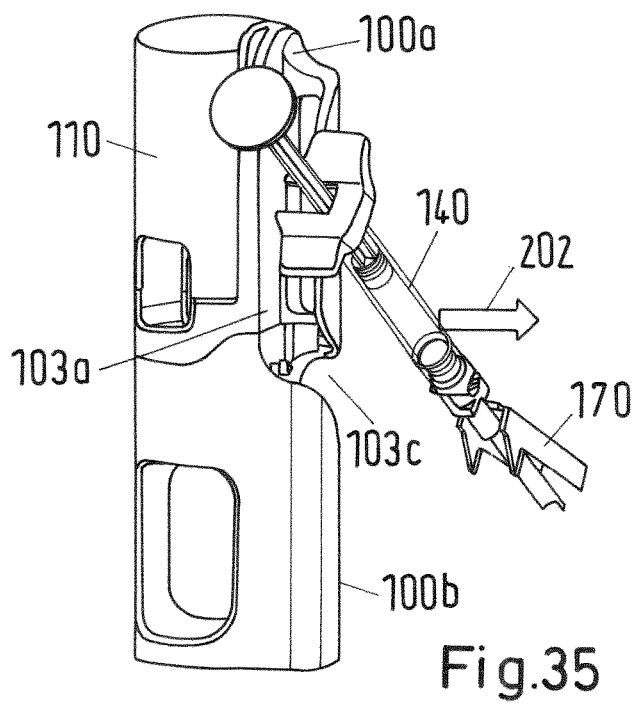
FIG. 35 shows a perspective side view of the system of FIG. 2 during a seventh step of the mixing and/or reconstitution method.

In order to administrate the mixed and/or reconstituted material 165 the syringe 140 is pulled from the adaptor 100 in horizontal direction as indicated by arrow 202 in FIG. 35. Further, the user may remove the needle cap prior using the syringe 140 for injection. By the removal of the syringe 140 form the adaptor 100 the valve 155 is released from the projections 106, 106a.

Figure 41:
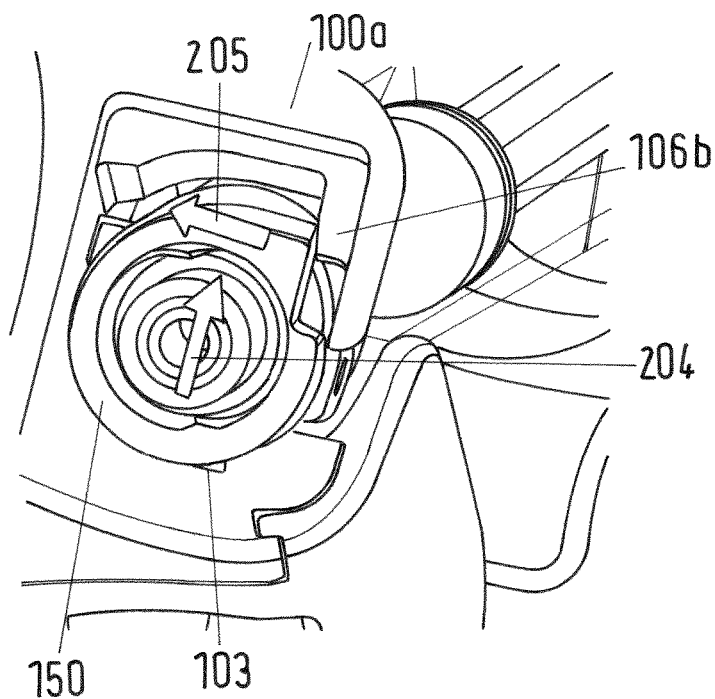
FIGS. 41-42 shows a sectional view of the system of FIG. 2 during assembly.
Figure 43:
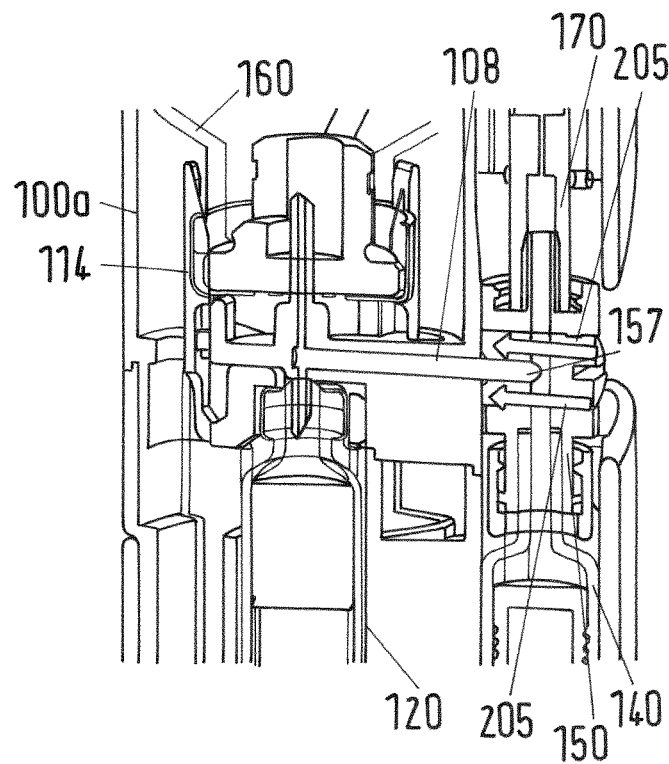
FIG. 43 shows a detail of the sectional view of FIG. 43.
Figure 42:
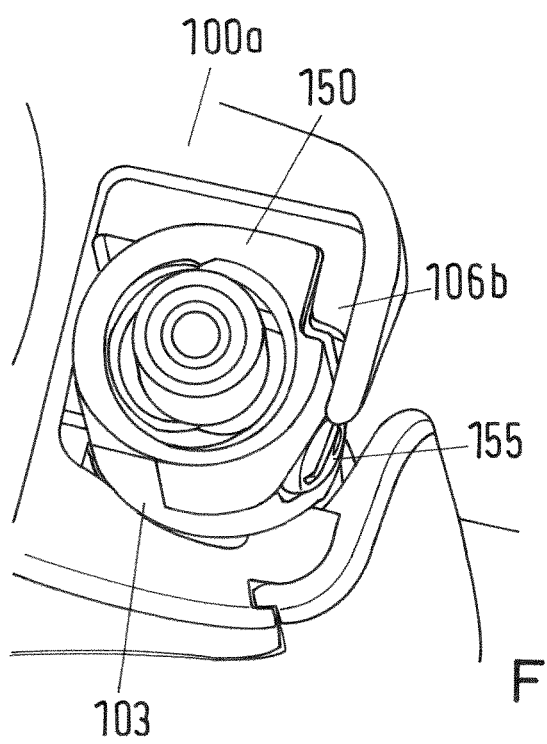

Finally, with regard to FIGS. 41 to 43 it shall be explained that during assembly of the system the attachment element 150 is fixed at the upper body 100a by a slant 106b which presses the attachment element 150 against the body 100a to seal the transition between the first channel 157 of the valve 155 and the vertical flow channel 108 of the upper body 100a and to provide a stiff connection between the syringe 140 and the adaptor 100.

Figure 44:
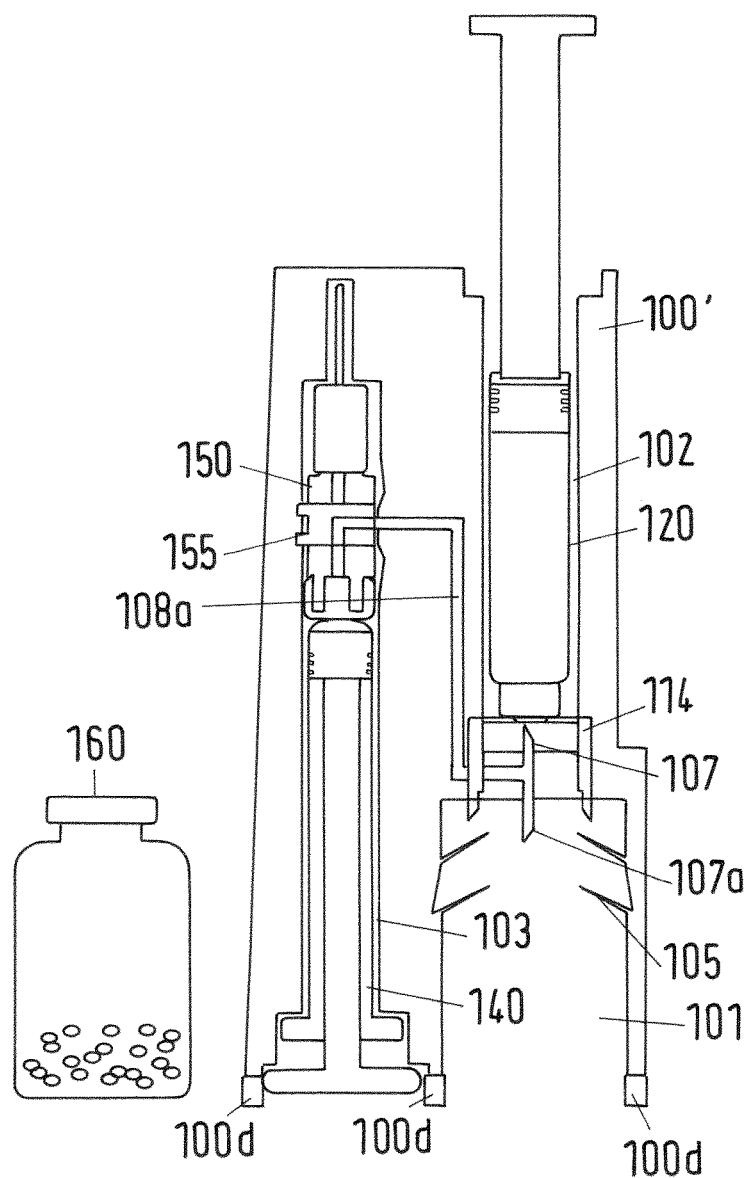
FIG. 44 shows a sectional view of a second embodiment of a mixing and/or reconstitution system with vial.
Figure 45:
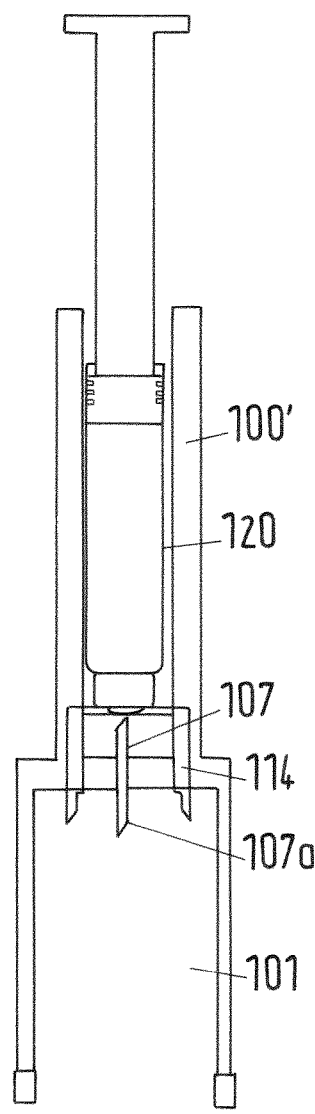
FIG. 45 shows another sectional view of the system of FIG. 44.
Figure 46:
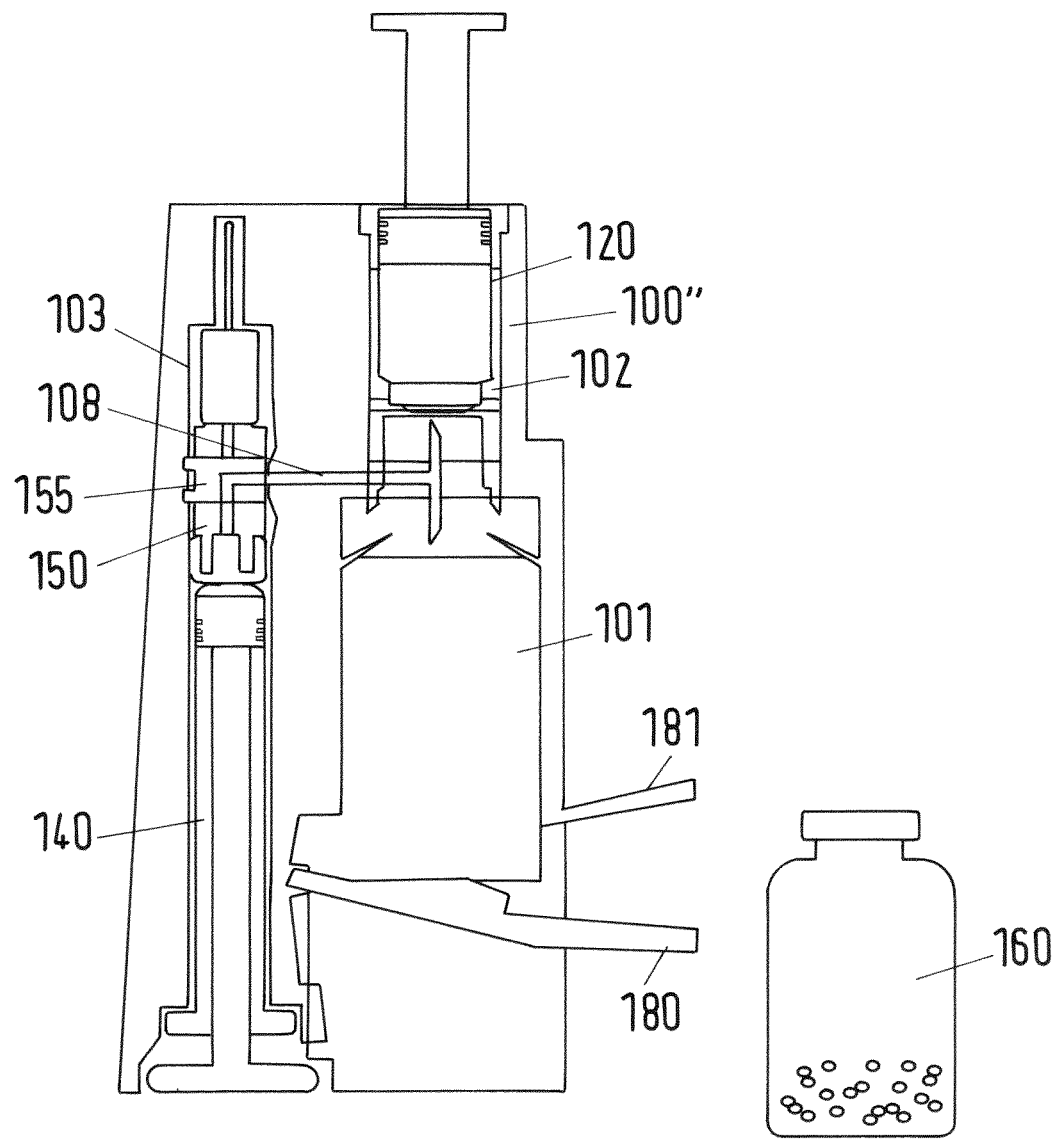
FIG. 46 shows a sectional view of a third embodiment of a mixing and/or reconstitution system with vial.

In FIGS. 44 and 45 a second embodiment of an system is depicted which basically works analogously to the first embodiment shown in FIGS. 1 to 43. The adaptor 100' of the second embodiment differs from the adaptor 100 shown in FIG. 1 therein that the flow channel 108a of the second embodiment has two horizontal sections and one vertical section whereas the flow channel 108 of the first embodiment is horizontal only and has no vertical section. The flow channel 108a of the second embodiment with the adaptor 100' is longer due to a misalignment of the syringe 140 and the double-ended needle 107. Additionally, this embodiment may further comprise anti-slip foot elements 100d provided at the lower end of adaptor 100'.

A third embodiment of an system is provided and depicted in FIGS. 46 to 49. The system of the third embodiment basically corresponds to the system depicted in FIG. 1. In contrast to the embodiment of FIG. 1 the syringe is provided within the third recess 103 in a reversed position. Further, the first recess 101 is provided with a swivel-mounted lever 180 on one side of its lower end and a handle 181 projecting laterally from the other side of its lower end.

Figure 47:
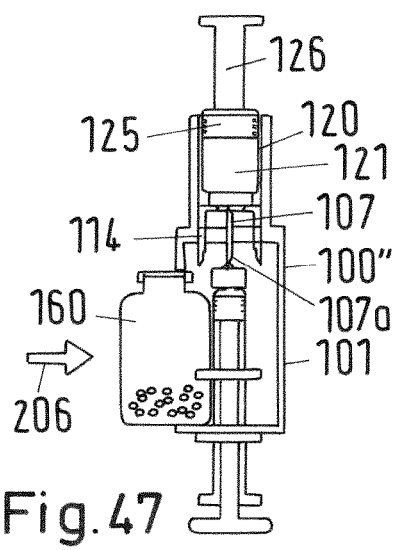
FIG. 47 shows a sectional view of the system of FIG. 46 during a first step of the mixing and/or reconstitution method.
Figure 48:
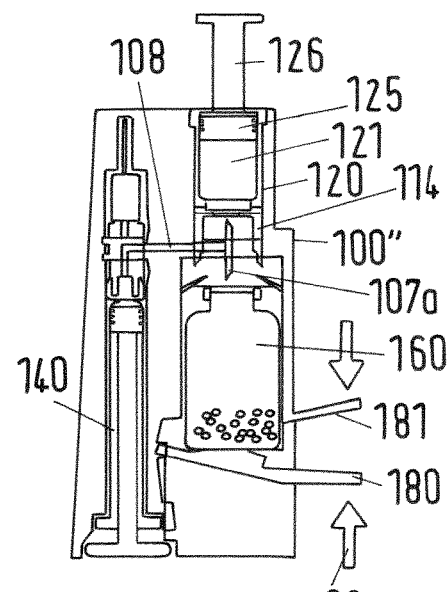
FIG. 48 shows a sectional view of the system of FIG. 46 during a second step of the mixing and/or reconstitution method.
Figure 49:
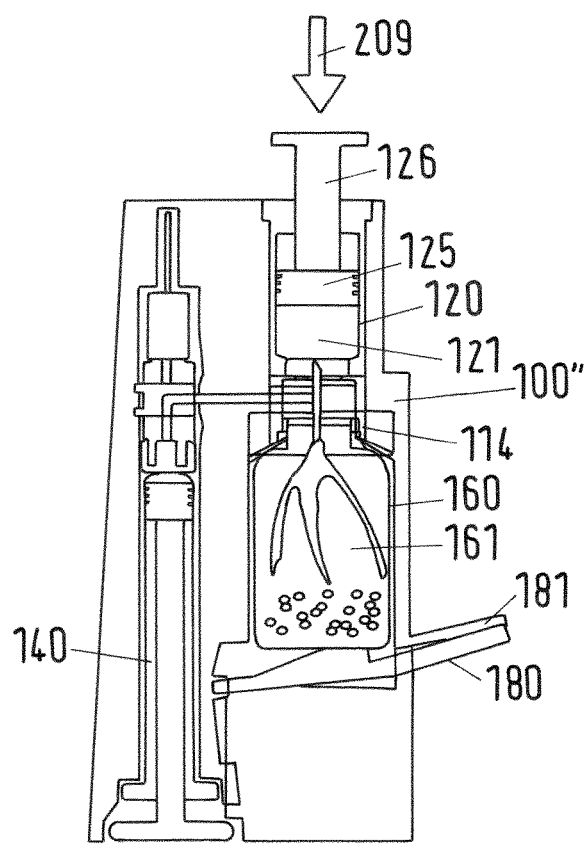
FIG. 49 shows a sectional view of the system of FIG. 46 during a third step of the mixing and/or reconstitution method.

In order to place the vial 160 within in the first recess of the adaptor 100" of the third embodiment the vial may be slid into the first recess 101 from the side as shown in FIG. 47 by arrow 206. In order to correctly position the vial 160 within the first recess 101 subsequently, as depicted in FIG. 48, the lever 208 is pivoted into the direction of the handle 181 as shown by arrow 208 in FIG. 48 thereby moving the vial 160 upwards into the direction of the lower end 107a of the needle 107. The final position of the vial within the first recess 101 is shown in FIG. 49. As soon as the pre-defined (correct) position is reached the cartridge protector 114 is triggered such that the cartridge 120 is allowed to move down into the direction of the needle 107 to establish a fluid connection between the cartridge reservoir 121 and the vial reservoir 161 by piercing the membrane of the cartridge 120. Afterwards, as shown in FIG. 49, a plunger 126 of the cartridge (instead of the plunger 110 of the adaptor as in the first embodiment) may be pressed downwards in order to establish this fluid connection and to empty the first material of the cartridge reservoir 121 into the vial reservoir 161. During these steps the lever 180 keeps closed with the handle 181 thereby fixing the vial 160 in the pre-defined (correct) position within the first recess 101.

Figure 50:
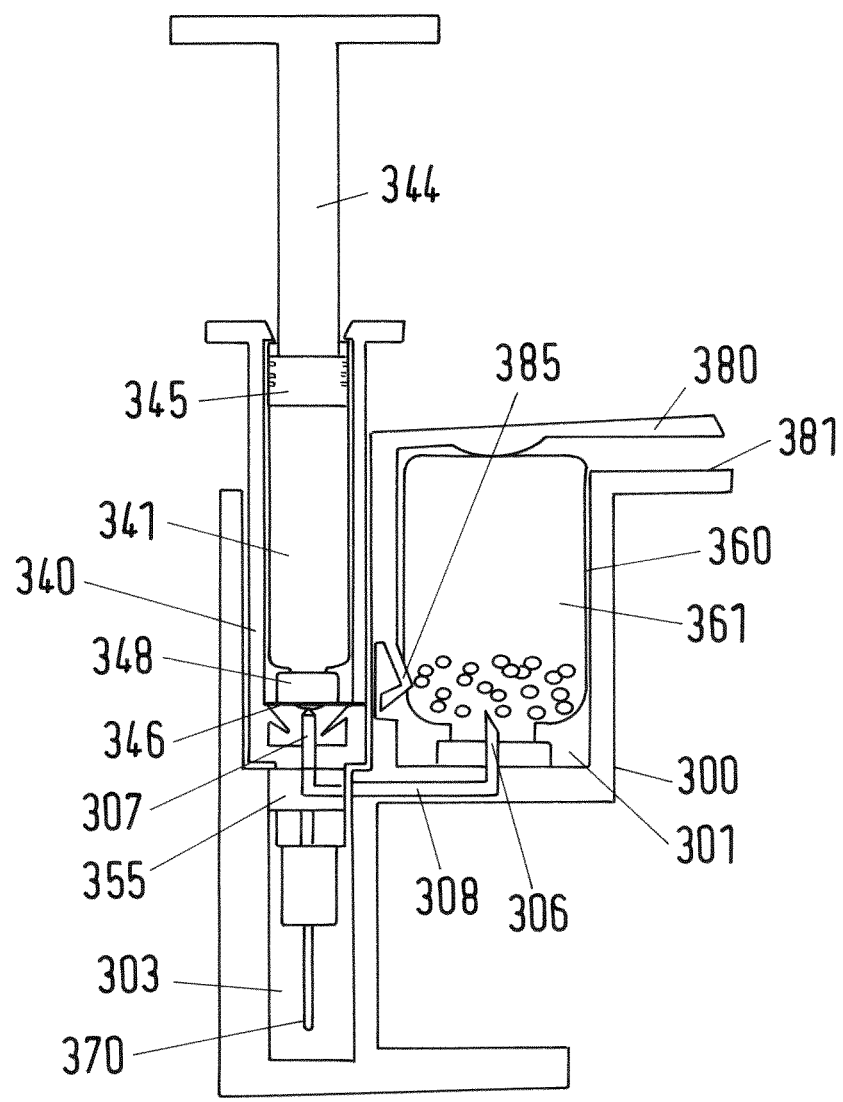
FIG. 50 shows a sectional view of a fourth embodiment of a mixing and/or reconstitution system with vial.
Figure 51:
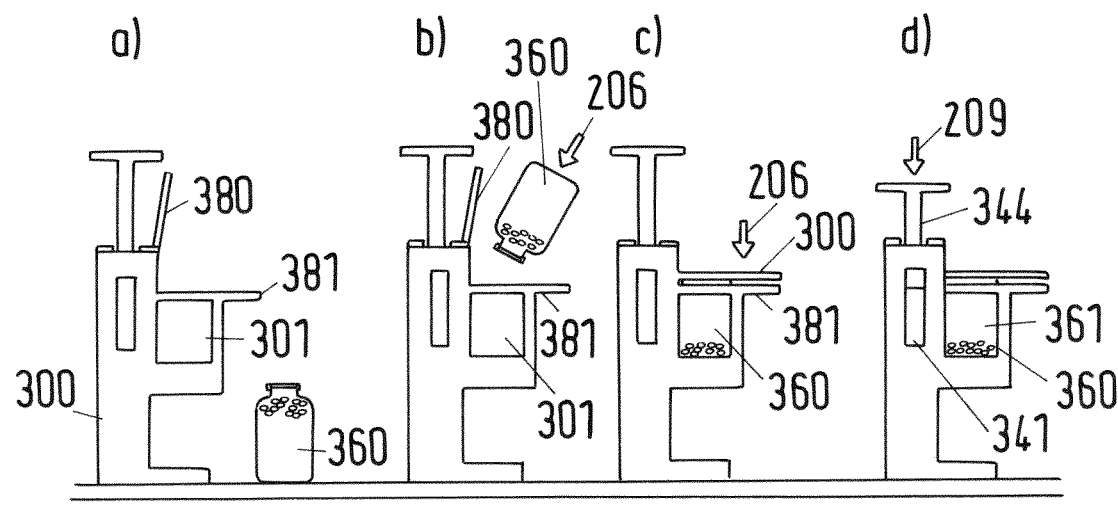
FIG. 51 shows a sectional view of the system of FIG. 50 in an initial state and during a first to third step of the mixing and/or reconstitution method.
Figure 52:
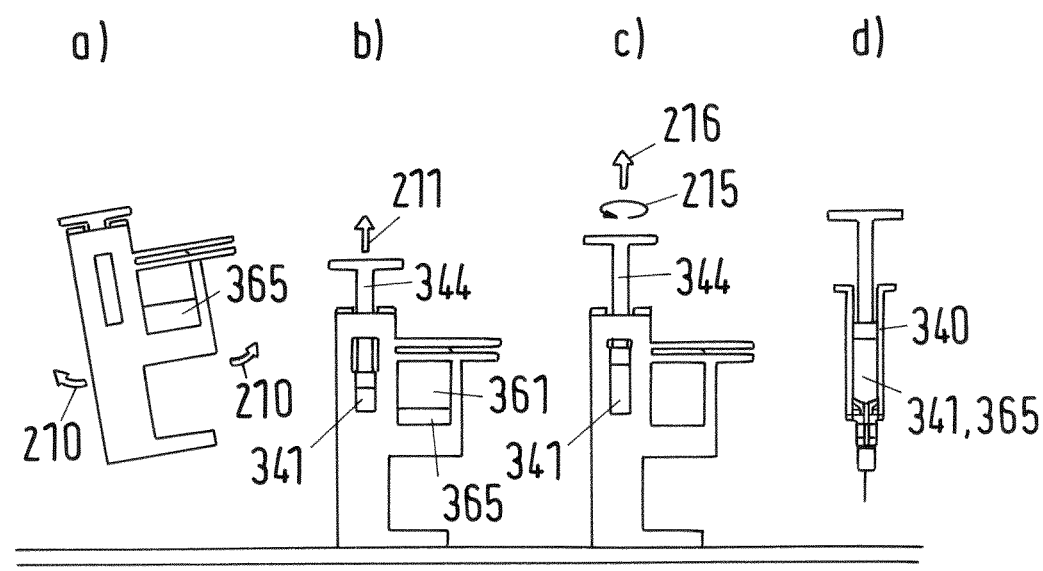
FIG. 52 shows a sectional view of the system of FIG. 50 during a fourth to seventh step of the mixing and/or reconstitution method.
Figure 53:
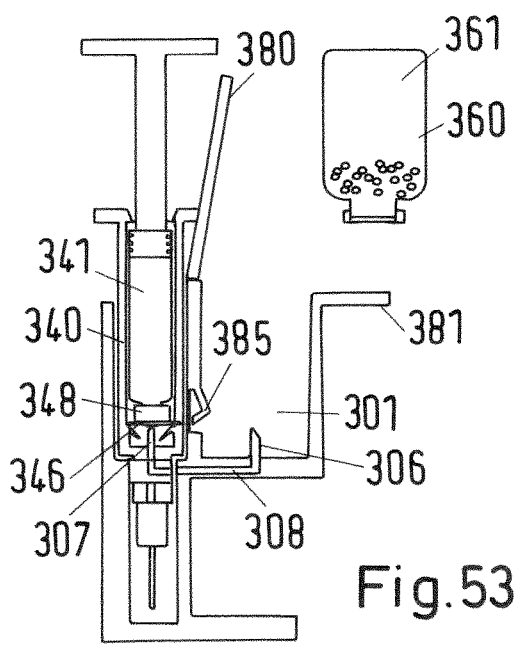
FIGS. 53-56 shows a sectional view of the system of FIG. 50 during the first to fourth step of the mixing and/or reconstitution method in more detail.

A fourth embodiment of an system and method is depicted in FIGS. 50 to 58 and 61 comprising an adaptor 300, an injection device 340 and a vial 360. In this embodiment the system does not comprise a cartridge separate from the injection device but is formed by the reservoir 341 of the cartridge of the injection device 340, wherein the cartridge is integrated in the injection device 340. Accordingly, the adaptor 300 comprises a first recess 301 and a second recess 303, wherein the first recess 301 is adapted to receive the vial 360 and the second recess accommodated in parallel to the first recess 301 is adapted to fix the injection device 340. As depicted in FIG. 50 the injection device 340 comprises analogously to the first embodiment a valve 355 within a vertical opening. Additionally, at the lower end of the injection device 340 a needle 370 is attached. The adaptor 300 further comprises at the lower end of the first recess 301 a needle 306 pointing upwards. The injection device 340 comprises a second needle 307 pointing upwards as well. In an initial state the second needle 307 does not pierce a membrane at an attachment portion 348 of the cartridge reservoir 341 which is ensured by a slider 346 supporting the attachment portion 348 and the cartridge reservoir 341. At its inner and lower side surface the first recess 301 comprises a leg 385 which is connected to the slider 346 of the injection device 340, wherein the leg 385 together with the slider 346 form the sensing arrangement for detecting a pre-defined position of the vial 360 within the first recess 301. The slider 346 forming the interlock element is shown in more detail in FIG. 61. The slider 346 supports the cartridge reservoir 341 and its attachment portion 348 in an initial state such that it has a pre-defined distance with regard to the upper end of the needle 307. The flow channel of the needle 306 is connected via a horizontal channel 308 within the adaptor 300 with the first channel 357 of the valve 355 (see FIG. 57a) and b) and FIG. 58) as a switching element and the flow channel of the needle 307.

The mixing and/or reconstitution method is now explained referring particularly to FIGS. 51 to 56.

Figure 54:
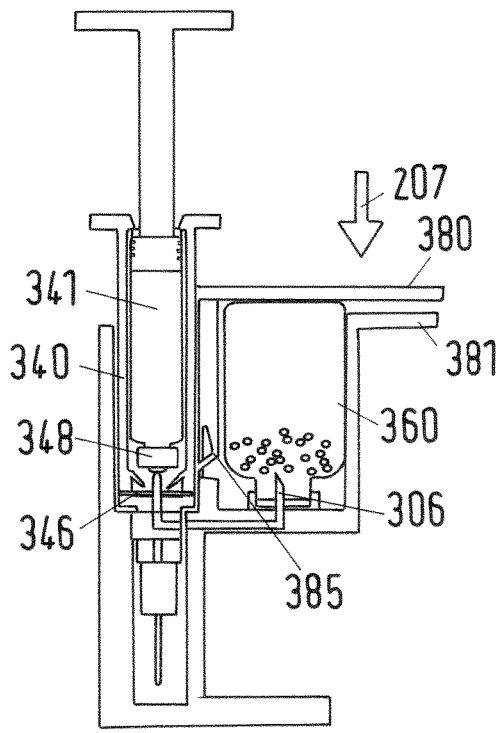
Figure 61:
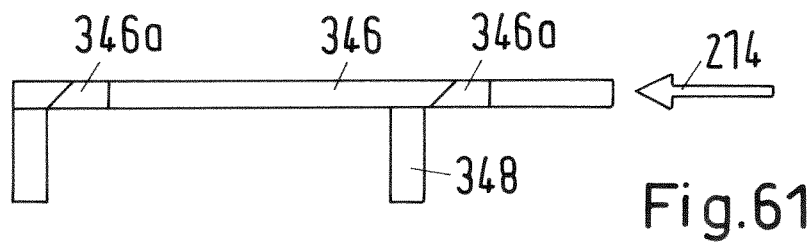
FIG. 61 shows a sectional view of the slider of the system of FIG. 50 in detail.

The initial state of the system according to this embodiment is depicted in FIG. 51a). For facilitating the mixing and/or reconstitution of the first fluid material contained in cartridge reservoir 341 and the second material contained in the vial reservoir 361 in the first step shown in FIG. 51b) the vial 360 is inserted into the first recess 301, wherein the cap of the vial 360 faces downwards. The movement direction of the vial 360 is depicted in FIG. 51b) by arrow 206. During insertion of the vial 360 the lever 380 is open (see FIG. 53). In order to position the vial 360 correctly within the first recess 301, afterwards, as shown in FIG. 51c) by arrow 207 the lever 380 is pivoted into the direction of handle 381 so that the recess 301 is closed thereby moving the vial 360 further downwards and pierce the membrane sealing the vial reservoir 361 by the needle 360. This step is shown in an enlarged drawing in FIG. 54. The FIG. 54 further shows that by the side wall of the vial 360 the leg 385 is pushed sideways into the direction of the injection device 340. Thereby, as shown in FIG. 61, the slider 346, which is connected to the leg 385, is moved horizontally as indicated by arrow 214 in FIG. 61. Hence, the slider 346 is moved so far that openings 346a within the slider (which were initially disengaged) now engage with respective projections 348 of the injection device 340 so that the slider 346 is allowed to move downwards. The final lower position of slider 346 is shown in FIG. 54.

Figure 55:
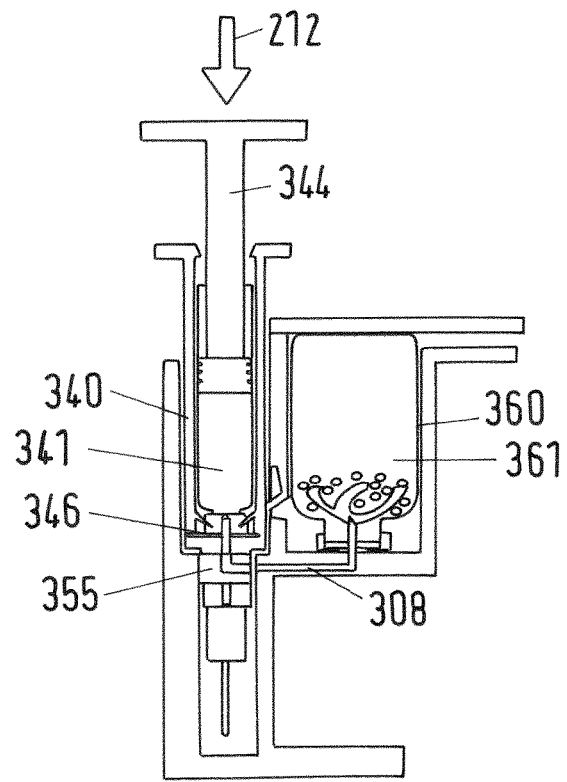

If now the user, if the slider 346 is in the lower position indicating that the vial is correctly at a pre-defined position adjusted within the first recess 301, presses the plunger 344 of the injection device as depicted in FIG. 51d) by arrow 209 or FIG. 55 by arrow 212 the attachment portion 348 and the cartridge reservoir 341 are moved down so that the needle 307 pierces the membrane sealing the cartridge reservoir 341 thereby establishing a fluid connection between the cartridge reservoir 341 and the vial reservoir 361. Accordingly, by further pressing the plunger 344 the first fluid material contained within the cartridge reservoir 341 is emptied via the flow channel of the needle 307, the first channel 357 of the valve 355, the horizontal flow channel 308 and the flow channel of the needle 306 into the vial reservoir 361 as depicted in FIG. 51d) and FIG. 55.

In the next step, the user may wait and slowly swivel (see arrows 210) the system in order to mix and/or reconstitute the first and second material within the vial reservoir 361 as shown in FIG. 52*a*).

Figure 56:
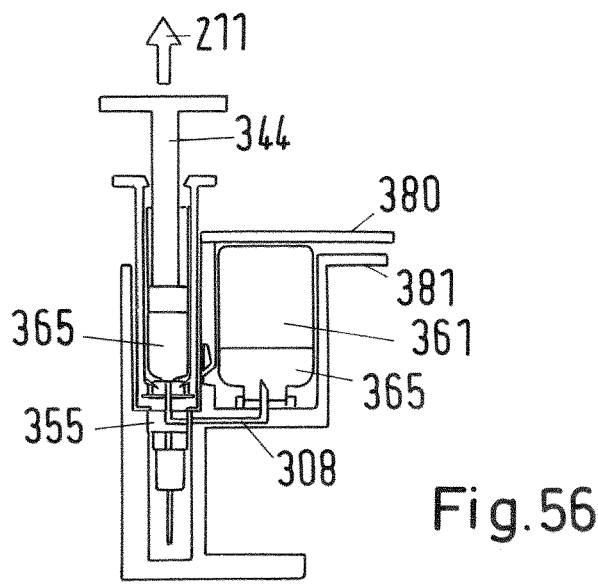

In the next step, as shown in FIG. 52*b*) the fully mixed and/or reconstituted material 365 is drawn back into the cartridge reservoir 341 by pulling the plunger 344 of the injection device 340 as depicted by arrow 211 in FIG. 52*b*). As one can derive from FIG. 56 showing the same step the mixed and/or reconstituted material 365 uses the same flow channel as in the step shown in FIG. 54. The mixing and/or reconstitution method is herewith finished providing a injection device filled with the mixed and/or reconstituted material 365.

Figure 57:
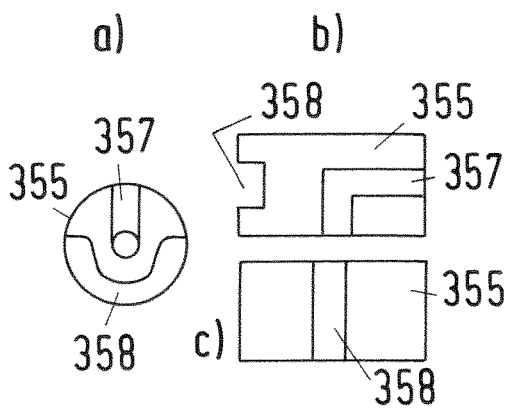
FIGS. 57-58 shows sectional views of the valve of the system of FIG. 50 in more detail.
Figure 58:
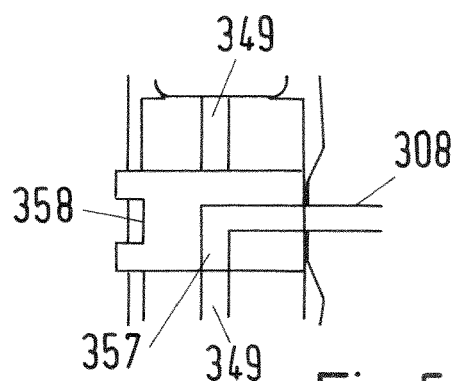
Figure 59:
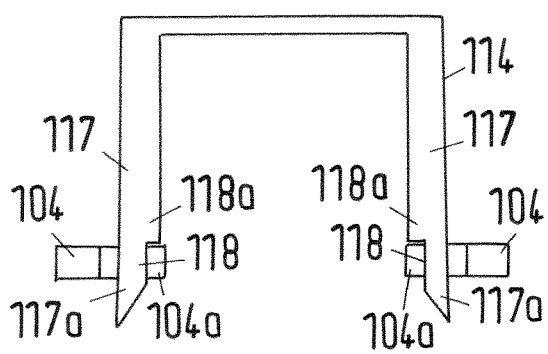
FIGS. 59-60 shows sectional views of another cartridge protector for use with the above systems.
Figure 60:
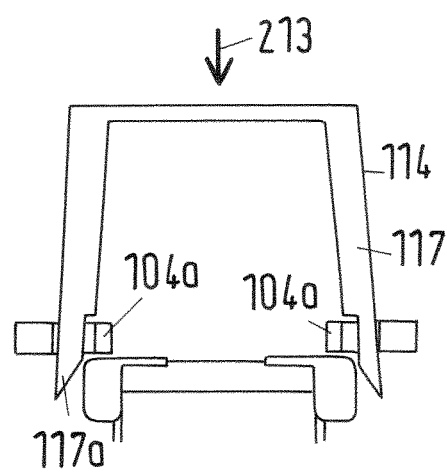

In order to administer the mixed and/or reconstituted material 365, afterwards, as depicted in FIG. 52*c*), the injection device is detached from the adaptor 300, for example by unscrewing the injection device and pulling (see arrows 215, 216). Now, as indicated in FIG. 52*d*) the injection device is ready to administrate the mixed and/or reconstituted material 365. For that the valve 355 must be switched into the second position, for example by a screw driver. Switching means, for example, rotation of the valve 355 with respect to the injection device 340 so that a second flow channel 358 connects the cartridge reservoir 341 and the needle 370 as depicted in FIGS. 57 and 58. The two-way selector valve 355 works analogously to the first embodiment shown in FIGS. 1 to 43. Unlike the first embodiment the valve 355 may be switched by an external tool.

LIST OF REFERENCE NUMBERS

100, 100', 100" adaptor
100*a* upper body
100*b* lower body
100*c* stop surface
100*d* foot element
101 first recess
102 second recess
103 third recess
103*a* third recess within the upper body 100*a*
103*b* third recess within the lower body 100*b*
103*c* intermediate portion
104 rib
104*a* projection
105 hook
106 projection
106*a* central projection
106*b* slant
107 double-ended needle
107*a* lower end of needle 107
107*b* de-aeration notch
108 horizontal flow channel
108*a* flow channel
109 vertical flow channel
110 plunger
110*a* web
110*b* lower end face of plunger 110
110*c* rod
111 handle
112 guard
113 snap fit
114 cartridge protector
115 flange
116 opening
117 leg
117*a* front end of leg
118 recess
118*a* edge
119 projection
120 cartridge
121 cartridge reservoir
122 cap
123 membrane
125 plug
126 plunger
140 syringe
141 syringe reservoir
143 handle
144 plunger
145 plug
148 attachment portion
150 attachment element
151 channel
152 attachment section
153 vertical opening
155 valve
156 longitudinal axis
157 first channel
158 second channel
159 recess
160 vial
161 vial reservoir
162 cap
163 membrane
165 mixture/constituted formulation
170 needle with protection element
180 lever
181 handle
191, 192, 193, 195, 198, 199, 200, 201, 202 arrow
203, 205, 206, 207, 208, 209, 210, 211, 212, 213 arrow
214, 215, 216 arrow
194, 196, 197, 201 dashed line
300 adaptor
301 first recess
303 second recess
306, 307 needle
308 flow channel
340 injection device
341 cartridge reservoir
344 plunger
345 plug
346 slider
346*a* opening
347 housing of the injection device 340
348 attachment portion
349 injection device channel
355 valve
357 first channel
358 second channel
360 vial
361 vial reservoir
365 mixture/constituted formulation
370 first needle
380 lever
381 handle
385 leg

The invention claimed is:

1. A system comprising:
   an adaptor,
   an integrated injection device removably attached to the adaptor, the injection device comprising
   a switching element, a first reservoir containing a first material, wherein the first material is a fluid, and a user-operatable trigger connected to the first reservoir, wherein the adaptor comprises:

a first attachment location, configured to attach a vial, a first connection element, a flow channel providing fluid communication between the switching element and the first connection element, a sensing arrangement configured to detect a pre-defined position of the vial at the first attachment location, and an interlock element that fixes the first reservoir in a pre-defined position relative to the adaptor to lock the trigger, the interlock element being configured to allow user operation of the trigger to establish fluid communication between the first connection element and the first reservoir only if the sensing arrangement detects the pre-defined position of the vial at the first attachment location.

2. The system of claim 1, wherein the first reservoir is provided by a cartridge of the injection device.

3. The system of claim 2, wherein the trigger comprises a plunger of the injection device, a plunger of the cartridge, or a longitudinally movable element of the adaptor connected to a plug of the cartridge.

4. The system of claim 1, wherein the first attachment location comprises a second connection element configured to establish fluid communication between the flow channel and a second reservoir of the vial during attachment of the vial at the first attachment location.

5. The system of claim 1, wherein the sensing arrangement is configured to detect a first state of the vial and a second state of the vial, wherein the second state is different from the first state and indicates that the vial is in the pre-defined position at the first attachment location.

6. The system of claim 1, wherein the first connection element is provided at a second attachment location.

7. The system of claim 6, wherein the second attachment location is a recess.

8. The system of claim 6, wherein the switching element is a two-way selector valve comprising:

a first channel, and a second channel, wherein the first channel is configured to provide fluid communication between the first reservoir of the injection device and the flow channel of the adaptor, wherein the second channel is configured to provide fluid communication between a needle of the injection device and the first reservoir of the injection device, and wherein the valve is configured to switch between the first channel and the second channel.

9. The system of claim 1, wherein the first connection element of the adaptor is within the injection device.

10. The system of claim 9, wherein the switching element is a two-way selector valve comprising:

an initial first channel, and a second channel, wherein the first channel is configured to provide fluid communication between the first connection element and the flow channel of the adaptor, wherein the second channel provides fluid communication between a needle of the injection device and the first connection element, and wherein the valve is configured to switch between the first channel and the second channel.

11. The system of any claim 1, wherein the adaptor comprises a de-aeration channel.

12. The system of claim 1, further comprising the vial containing a second material within a second reservoir, wherein the second material contains a medicament formulation.

13. The system of claim 1, wherein the first attachment location is a recess.

14. The system of claim 1, wherein the vial contains a second material within a second reservoir, wherein the second material contains a medicament formulation.

15. The system of claim 1, wherein the first attachment location is formed as a recess within the adaptor, the recess guiding the vial into the pre-defined position of the vial at the first attachment location.

* * * * *

UNITED STATES PATENT AND TRADEMARK OFFICE
CERTIFICATE OF CORRECTION

PATENT NO. : 11,752,070 B2
APPLICATION NO. : 16/765226
DATED : September 12, 2023
INVENTOR(S) : Sarah Helm et al.

It is certified that error appears in the above-identified patent and that said Letters Patent is hereby corrected as shown below:

In the Claims

In Column 22, Line 26 (approx.), Claim 11, delete "of any" and insert -- of --

Signed and Sealed this
Thirty-first Day of October, 2023

Katherine Kelly Vidal
*Director of the United States Patent and Trademark Office*